(12) United States Patent
Linderman et al.

(10) Patent No.: US 9,795,429 B2
(45) Date of Patent: *Oct. 24, 2017

(54) DEVICE AND METHOD FOR REMOVING BODILY MATERIAL

(71) Applicant: Stryker Corporation, Kalamazoo, MI (US)

(72) Inventors: Evan D. Linderman, Deerfield, IL (US); John A. Krueger, Muskego, WI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/076,221

(22) Filed: Mar. 21, 2016

(65) Prior Publication Data

US 2016/0199097 A1 Jul. 14, 2016

Related U.S. Application Data

(60) Continuation of application No. 14/223,064, filed on Mar. 24, 2014, now Pat. No. 9,358,059, which is a (Continued)

(51) Int. Cl.
*A61B 17/16* (2006.01)
*A61B 17/34* (2006.01)
(Continued)

(52) U.S. Cl.
CPC ...... *A61B 17/8819* (2013.01); *A61B 17/8811* (2013.01); *A61B 17/1604* (2013.01); (Continued)

(58) Field of Classification Search
CPC ............ A61B 17/8819; A61B 17/8811; A61B 17/1604; A61B 17/1671; A61B 17/3421; A61B 17/3472; A61B 17/8836; A61B 2090/062; A61B 2019/462; A61B 2017/00331; A61B 2017/00455; A61B 2017/00867
USPC ................ 606/92–94, 264; 604/272, 164.01, 604/164.11, 187, 95.01, 82, 264, 506; 433/224; 222/386.5, 399; 623/23.62
See application file for complete search history.

(56) References Cited

U.S. PATENT DOCUMENTS 4,265,231 A 5/1981 Scheller, Jr. et al.
5,295,980 A 3/1994 Ersek
(Continued)

FOREIGN PATENT DOCUMENTS

EP 1459691 A1 9/2004
WO WO 9856301 A1 12/1998

*Primary Examiner* — Pedro Philogene
(74) *Attorney, Agent, or Firm* — Howard & Howard Attorneys PLLC

(57) ABSTRACT

A cannula device for removing, including by aspirating, bodily material is disclosed. The device may include a cannula and a hub. The cannula includes an open proximal end and a deflectable distal segment, and one or a plurality of distal orifices fluidly connected to the lumen. When distally extended from an outer guide cannula, the deflectable segment assumes a curved shape, which includes temperature-dependent curvature subject to elevated temperature along a memory metal length of the cannula.

22 Claims, 14 Drawing Sheets

Related U.S. Application Data continuation of application No. 13/483,899, filed on May 30, 2012, now Pat. No. 8,690,884, which is a continuation-in-part of application No. 12/633,358, filed on Dec. 8, 2009, now Pat. No. 8,529,576, which is a division of application No. 11/704,139, filed on Feb. 8, 2007, now Pat. No. 7,799,035, which is a continuation-in-part of application No. 11/282,102, filed on Nov. 18, 2005, now Pat. No. 7,713,273.

(51) Int. Cl.
*A61B 17/88* (2006.01)
*A61B 17/00* (2006.01)
*A61B 90/00* (2016.01)

(52) U.S. Cl.
CPC ....... *A61B 17/1671* (2013.01); *A61B 17/3421* (2013.01); *A61B 17/3472* (2013.01); *A61B 17/8836* (2013.01); *A61B 2017/00331* (2013.01); *A61B 2017/00455* (2013.01); *A61B 2017/00867* (2013.01); *A61B 2090/062* (2016.02)

(56) References Cited

U.S. PATENT DOCUMENTS

| | | |
|---|---|---|
| 5,609,629 A | 3/1997 | Fearnot et al. |
| 5,732,698 A | 3/1998 | Swanson et al. |
| 5,843,103 A | 12/1998 | Wulfman |
| 5,851,209 A | 12/1998 | Kummer et al. |
| 5,879,353 A | 3/1999 | Terry |
| 5,891,147 A | 4/1999 | Moskovitz et al. |
| 5,928,239 A | 7/1999 | Mirza |
| 5,972,015 A | 10/1999 | Scribner et al. |
| 6,048,346 A | 4/2000 | Reiley et al. |
| 6,066,154 A | 5/2000 | Reiley et al. |
| 6,241,734 B1 | 6/2001 | Scribner et al. |
| 6,248,110 B1 | 6/2001 | Reiley et al. |
| 6,296,639 B1 | 10/2001 | Truckai et al. |
| 6,328,744 B1 | 12/2001 | Harari et al. |
| 6,358,251 B1 | 3/2002 | Mirza |
| 6,383,188 B2 | 5/2002 | Kuslich et al. |
| 6,383,190 B1 | 5/2002 | Preissman |
| 6,425,887 B1* | 7/2002 | McGuckin ......... A61B 17/3417 604/272 |
| 6,440,138 B1 | 8/2002 | Reiley et al. |
| 6,494,868 B2 | 12/2002 | Amar |
| 6,575,978 B2 | 6/2003 | Peterson et al. |
| 6,592,559 B1 | 7/2003 | Pakter et al. |
| 6,641,587 B2 | 11/2003 | Scribner et al. |
| 6,645,213 B2 | 11/2003 | Sand et al. |
| 6,676,664 B1 | 1/2004 | Al Assir |
| 6,679,886 B2 | 1/2004 | Weikel et al. |
| 6,740,090 B1 | 5/2004 | Cragg et al. |
| 6,746,451 B2 | 6/2004 | Middleton et al. |
| 6,783,515 B1 | 8/2004 | Miller et al. |
| 6,790,210 B1 | 9/2004 | Cragg et al. |
| 6,793,660 B2 | 9/2004 | Kerr et al. |
| 6,814,734 B2 | 11/2004 | Chappuis et al. |
| 6,843,796 B2 | 1/2005 | Harari et al. |
| 6,863,672 B2 | 3/2005 | Reiley et al. |
| 6,875,219 B2 | 4/2005 | Arramon et al. |
| 6,921,403 B2 | 7/2005 | Cragg et al. |
| 6,923,813 B2 | 8/2005 | Phillips et al. |
| 7,004,945 B2 | 2/2006 | Boyd et al. |
| 7,025,771 B2 | 4/2006 | Kuslich et al. |
| 7,048,743 B2 | 5/2006 | Miller et al. |
| 7,066,942 B2 | 6/2006 | Treace |
| 7,087,040 B2* | 8/2006 | McGuckin, Jr. ....... A61B 18/00 604/158 |
| 7,087,058 B2 | 8/2006 | Cragg |
| 7,114,501 B2 | 10/2006 | Johnson et al. |
| 7,682,378 B2 | 3/2010 | Truckai et al. |
| 7,713,273 B2* | 5/2010 | Krueger ............. A61B 17/8811 606/92 |
| 7,799,035 B2* | 9/2010 | Krueger ............. A61B 17/8811 606/92 |
| 8,128,633 B2 | 3/2012 | Linderman et al. |
| 8,690,884 B2* | 4/2014 | Linderman ........ A61B 17/8811 606/94 |
| 9,358,059 B2* | 6/2016 | Linderman ........ A61B 17/8811 |
| 2002/0099384 A1 | 7/2002 | Scribner et al. |
| 2002/0120240 A1* | 8/2002 | Bagga ................ A61B 17/1671 604/264 |
| 2002/0156483 A1 | 10/2002 | Voellmicke et al. |
| 2003/0036762 A1 | 2/2003 | Kerr et al. |
| 2003/0078589 A1 | 4/2003 | Preissman |
| 2004/0068264 A1* | 4/2004 | Treace ............... A61B 17/1635 606/86 R |
| 2004/0068267 A1 | 4/2004 | Harvie et al. |
| 2004/0162559 A1* | 8/2004 | Arramon ............ A61B 17/3417 606/62 |
| 2004/0215202 A1 | 10/2004 | Preissman |
| 2005/0038432 A1 | 2/2005 | Shaolian et al. |
| 2005/0070913 A1 | 3/2005 | Milbocker et al. |
| 2006/0009779 A1 | 1/2006 | Collins et al. |
| 2006/0064101 A1* | 3/2006 | Arramon .......... A61B 17/32002 606/82 |
| 2006/0116643 A1 | 6/2006 | Dixon |
| 2006/0149280 A1 | 7/2006 | Harvie et al. |
| 2006/0195094 A1 | 8/2006 | McGraw et al. |
| 2006/0217736 A1 | 9/2006 | Kaneko et al. |
| 2006/0241624 A1 | 10/2006 | Kizuka et al. |
| 2006/0264967 A1 | 11/2006 | Ferreyro et al. |
| 2011/0046737 A1 | 2/2011 | Teisen |
| 2011/0112507 A1 | 5/2011 | Linderman et al. |
| 2011/0245926 A1 | 10/2011 | Kitchen |
| 2012/0016371 A1 | 1/2012 | O'Halloran et al. |

* cited by examiner

DEVICE AND METHOD FOR REMOVING BODILY MATERIAL

RELATED APPLICATIONS

This application is a continuation of co-pending U.S. application Ser. No. 14/223,064, which is a continuation of co-pending U.S. application Ser. No. 13/483,899, which is a continuation-in-part of U.S. patent application Ser. No. 12/633,358, filed Dec. 8, 2009 (now issued as U.S. Pat. No. 8,529,576), which is a divisional of U.S. application Ser. No. 11/704,139, filed Feb. 8, 2007 (now issued as U.S. Pat. No. 7,799,035), which is a continuation-in-part of U.S. application Ser. No. 11/282,102, filed Nov. 11, 2005 (now issued as U.S. Pat. No. 7,713,273), each of which is incorporated by reference herein in its entirety, and to which priority is claimed.

TECHNICAL FIELD

The present invention relates to devices and methods for stabilizing bone structures. More particularly, it relates to systems and methods for delivering a curable, stabilizing material into a bone structure.

BACKGROUND

Surgical intervention at damaged or compromised bone sites has proven highly beneficial for patients, for example patients with back pain associated with vertebral damage.

Bones of the human skeletal system include mineralized tissue that can generally be categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae."

During certain bone procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement). In other procedures, percutaneous injection of stabilization material into vertebral compression fractures by, for example, transpedicular or parapedicular approaches, has proven beneficial in relieving pain and stabilizing damaged bone sites. Other skeletal bones (e.g., the femur) can be treated in a similar fashion. In any regard, bone in general, and cancellous bone in particular, can be strengthened and stabilized by a palliative injection of bone-compatible material.

The conventional technique for delivering the bone stabilizing material entails employment of a straight access device or cannula that bores (or otherwise cuts) through the cortical bone to gain access to the cancellous bone site. Bone stabilization material is then driven through the cannula to fill a portion of the cancellous bone at the bone site. To minimize invasiveness of the procedure, the cannula is typically a small diameter needle.

With the above in mind, because the needle cannula interacts with the cancellous bone and other soft tissue structures, an inherent risk exists that following initial insertion, the needle cannula might core or puncture other tissue and/or the bone mass being repaired (at a location apart from the insertion site). Thus, during percutaneous vertebroplasty, great care must be taken to avoid puncturing, coring, or otherwise rupturing the vertebral body. Similar post-insertion coring concerns arise in other interior bone repair procedures. Along these same lines, to minimize trauma and time required to complete the procedure, it is desirable that only a single bone site insertion be performed. Unfortunately, for many procedures, the surgical site in question cannot be fully accessed using a conventional, straight needle cannula. For example, with vertebroplasty, the confined nature of the inner vertebral body oftentimes requires two or more insertions with the straight needle cannula at different vertebral approach locations ("bipedicular" technique). It would be desirable to provide a system for delivering bone stabilizing material that can more readily adapt to the anatomical requirements of a particular delivery site, for example a system capable of promoting unipedicular vertebroplasty.

Certain instruments utilize a curved needle to deliver bone stabilizing material as part of vertebroplasty or similar procedure. The curved needle purportedly enhances a surgeon's ability to locate and inject the stabilizing material at a desired site. Similar to a conventional straight needle cannula, the curved needle dispenses the curable material through a single, axial opening at the distal-most tip. However, the curved needle is used in combination with an outer cannula that assists in generally establishing access to the bone site as well as facilitating percutaneous delivery of the needle to the delivery site (within bone) in a desired fashion. More particularly, the outer cannula first gains access to the bone site, followed by distal sliding of the needle through the outer cannula. After the needle's tip extends distal a distal end of the outer cannula, the needle tip is "exposed" relative to the bone site. To avoid coring, and thus potentially damaging, tissue when inserting the needle's distal tip into the bone site, an additional wire component is required, coaxially disposed within the needle and distally extending from the distal tip. The inner wire "protects" tissue or other bodily structures from traumatically contacting the distal tip of the needle as the tip is being positioned. The coaxial wire must be removed prior to infusing the bone stabilizing material through the needle.

Further, the needle can only dispense the stabilizing material through the axial opening at the distal tip of the needle, perhaps impeding a surgeon's ability to infuse all desired areas and/or requiring an additional procedural step of "backing" the needle tip away from the desired delivery site. Also, because the needle tip, and thus the axial opening, is likely at or facing the bone defect (e.g., fracture in the vertebral body) being repaired, the stabilizing material may be injected directly at the defect, giving rise to a distinct possibility that the stabilizing material will forcibly progress through and outwardly from the defect. This is clearly undesirable. The issues and concerns described above in the context of percutaneous vertebroplasty can also arise in similar surgical procedures at other bone sites.

The injection of palliative materials into damaged or compromised bone sites has proven highly beneficial for patients. However, the known access and infusion techniques necessitate multiple needle sticks and/or risk coring bone or tissue. Also, curved needles may suffer stress and/or binding within the lumen of guide cannulas and/or may include a pre-set curve that does not provide for desired access to a targeted injection site. Providing many different needles with different curvatures adds medical expense borne by patients and/or insurers, and the need to exchange a needle for one with a different curvature increases procedure time (which may, for example, add patient time under anesthesia, increase cost for operating suite time usage). Therefore, a need exists for an improved device and system for delivering stabilizing material to damaged or compromised bone sites.

BRIEF SUMMARY

Embodiments disclosed herein may include a delivery cannula providing a non-traumatic, blunt distal end that minimizes the risks of coring tissue or puncturing bone or tissue during intraosseous procedures without requiring additional components (such as separate wire). Certain embodiments relate to vertebroplasty systems including guide cannula, delivery cannula, which may be embodied as a needle and that may be formed of or at least include a memory metal, where the memory metal is configured to be generally straight at ambient temperature and to be manipulable to at least a first curve at a first higher selected temperature and a second curve at a second higher selected temperature. Certain embodiments may relate to a delivery cannula defining at least one side orifice adjacent to a blunt distal end, where the orifice(s) permit a radial infusion of a curable material at a site within bone even in the case where the distal end is in contact with bone and/or tissue. Thus, a palliative bone procedure can be accomplished with reduced operating room time and with fewer approaches of surgical instruments to the bone site. For example, unipedicular vertebroplasty may readily be accomplished. Further, virtually any area within the surgical site may be accessible with less time and effort than would be required with one or more needles having only a single pre-set curve. Also, the distal end of the delivery cannula can be placed as close as desired to a particular anatomical feature of the surgical site (e.g., a bone fracture) without fear that subsequently delivered material will forcibly progress into or through that feature. It should be appreciated that the present embodiments are readily adaptable within the art to be used in other bone augmentation procedures.

Some aspects of the presently disclosed embodiments may relate to a delivery cannula device for delivering a curable material into bone. The device includes a delivery cannula and a hub forming a fluid port. The delivery cannula defines a proximal end, a deflectable segment including a memory metal material, a distal end, a lumen, and at least one side orifice. The proximal end is axially open to the lumen. The deflectable segment is formed opposite the proximal end and terminates at the distal end that is otherwise axially closed. Further, the distal end has a blunt tip. The lumen extends from the proximal end and is fluidly connected to the side orifice(s). To this end, the side orifice(s) is formed adjacent to, and proximally space from, the distal end. Finally, the deflectable segment including a memory metal material may be actuated by predetermined application of a selected heat energy to form at least a first curved shape and a second curved shape in longitudinal extension as it has a temperature-dependent multi-state curvature shape memory characteristic. With this configuration, the deflectable segment begins in a substantially straightened shape at ambient temperature and will assume the first, second, and/or other curved shape upon provision of heat energy to provide a corresponding temperature. The hub is fluidly coupled to the proximal end of the delivery catheter. With this construction and during use, the distal end will not damage or core tissue when inserted into a delivery site within bone due to the blunt tip. Further, the side orifice(s) afford the ability to inject a curable material regardless of whether the distal end is lodged against bodily material, and can achieve more thorough dispensing.

Other aspects of the presently-disclosed embodiments may relate to an intraosseous, curable material delivery system for delivering a curable material, such as bone cement, to a delivery site within bone. The system includes the delivery cannula and hub as described in the previous paragraph, along with a guide cannula. The delivery cannula and the guide cannula are sized such that the delivery cannula is slidable within the guide cannula. To this end, the deflectable segment is configured to maintain a substantially straight-line shape when inserted within the cannula and be actuatable to the first, second, and/or further curved shapes when extended distal the guide cannula for delivery of the curable material and heated to corresponding first, second, and/or further temperatures. In one embodiment, the guide cannula and the delivery cannula may be sized to perform a vertebroplasty procedure.

Yet other aspects of the presently disclosed embodiments may relate to methods of stabilizing a bone structure of a human patient. The method includes providing a delivery cannula as previously described. A distal tip of a guide cannula is located within the bone structure. The delivery cannula is inserted within the guide cannula. In this regard, the deflectable segment begins in a substantially straightened shape within the guide cannula at a typical ambient temperature (defined herein as being at or below patient body temperature and generally within a range typical for a hospital operating room or similar environment, e.g., about 15° C. to about 38° C., preferably about 20° C. to about 23° C.). The delivery cannula is distally advanced relative to the guide cannula such that the distal end and at least a portion of the deflectable segment of the delivery cannula projects distal the distal tip of the guide cannula. To this end, the portion of the deflectable segment distal the distal tip of the guide cannula may be actuated to a selected, temperature-dependent one of two or more curved shapes by providing heat energy to establish a cannula temperature corresponding to the desired curvature. The distal end of the delivery cannula is positioned adjacent a desired delivery site within the bone structure. A curable material is injected into the lumen. The injected curable material is delivered to the delivery site via the side orifice(s). After it has been delivered, the curable material is allowed to cure so as to stabilize the bone structure. In one embodiment, the method further includes rotating the delivery cannula relative to the guide cannula so as to alter a spatial position of the side orifice(s), thus affording the ability to inject the curable material in different planes.

Still another aspect of the presently disclosed embodiments may relate to methods of injecting curable material to a delivery site within a bone structure. The methods may include steps of providing a delivery cannula having an open, proximal end, a deflectable segment opposite the proximal end having a distal end, and a lumen extending from the proximal end. The deflectable segment has a shape memory characteristic and may be heat-actuated to assume a first, second, and/or further curved shape in longitudinal extension. The method may also include a step of locating a distal tip of a guide cannula within the bone structure. The method may further include a step of inserting the delivery cannula within the guide cannula, when the deflectable segment is in a default substantially straightened shape within the guide cannula, and distally advancing the delivery cannula such that the distal end and at least a portion of the deflectable segment projects distal the distal tip. The portion of the deflectable segment distal the distal tip then may be heated to a selected temperature corresponding to a desired curve. The method may also include a step of manipulating the delivery cannula such that at least a portion of the deflectable segment (when straight, and/or when curved) creates one or more voids in soft body tissue within the bone structure. The method may also include a step of delivering the curable material to the delivery site wherein the curable material is delivered to the one or more voids in the soft body tissue created by the deflectable segment.

Yet another aspect of the presently disclosed embodiments may relate to a method of injecting curable material to a delivery site within a bone structure. The method includes the step of providing a delivery cannula having an open, proximal end, a deflectable segment opposite the proximal end having a distal end and a lumen extending from the proximal end. The deflectable segment has a shape memory characteristic and will, when heated to a corresponding selected temperature assume a first, second, and/or further curved shape in longitudinal extension. In the method, the distal tip of a guide cannula may be located within the bone structure. The delivery cannula is inserted within the guide cannula, where the deflectable segment is, at an ambient temperature, in a substantially straightened shape within the guide cannula. The delivery cannula is distally advanced such that the distal end and at least a portion of the deflectable segment projects distal the distal tip, whereafter the portion of the deflectable segment distal the distal tip may assume the first, second, and/or further curved shape upon application of heat energy to provide a corresponding temperature. The distal end is positioned distally adjacent a first region within the delivery site. The curable material is then delivered to the first region within the delivery site. The distal end is then positioned adjacent a second region within the delivery site and curable material is delivered to the second region within the delivery site. The second site may be accessed using the same cannula curvature as the first site, or the cannula may be heated to a different temperature corresponding to a different curvature to access a different second region.

Yet another aspect of the presently disclosed embodiments may relate to a cannula device for delivering a curable material, such as bone cement, into bone as part of a curable material delivery system. The device includes a delivery cannula preloaded with bone cement, with the cannula including an open, proximal end, a deflectable segment opposite the proximal end and terminating in a closed distal end. The device also includes a lumen extending from the proximal end to at least one side orifice formed adjacent to, and proximally spaced from, the distal end. The deflectable segment forms a curved shape in longitudinal extension after being heated, as it has a shape memory characteristic such that it is configured to assume a longitudinally, substantially straightened form when at ambient temperature and at least two curved shapes, each corresponding to a different selected higher temperature.

In yet another aspect some presently disclosed embodiments relate to methods of injecting curable material within a bone structure, some method comprising: providing a delivery cannula defining: an open, proximal end, a distal segment opposite the proximal end having a distal end, a lumen extending from the proximal end; locating a distal tip of a guide cannula within the bone structure; inserting the delivery cannula within the guide cannula; distally advancing the delivery cannula such that the distal end projects distal of the distal guide cannula tip; heating the delivery cannula to a first temperature to actuate it to a first selected curvature; positioning the distal end distally adjacent a first region within the delivery site; delivering the curable material to the first region within the delivery site; positioning the distal end distally adjacent a second region within the delivery site without removing the guide cannula from the bone structure; delivering the curable material to the second region within the delivery site; and delivering the curable material to a third region within the delivery site between and connecting the first and second regions. The method may further include heating the delivery cannula to a second temperature to actuate it to a second selected curvature before or after positioning the distal end distally adjacent the second region; and, if after, may provide for accessing the third region within the delivery site.

Yet another aspect of the presently disclosed embodiments may relate to a method of injecting curable material within a bone structure, the method comprising: providing a delivery cannula defining: an open proximal end, a distal segment opposite the proximal end having a distal end, a lumen extending from the proximal end; locating a distal tip of a guide cannula within the bone structure; inserting the delivery cannula within the guide cannula; distally advancing the delivery cannula such that the distal end projects distal of the distal tip; heating the delivery cannula to a first temperature to actuate it to a first selected curvature; positioning the distal end distally adjacent a first region within the delivery site; delivering the curable material to the first region within the delivery site; positioning the distal end distally adjacent a second region within the delivery site without removing the guide cannula from the bone structure; and delivering the curable material to the second region within the delivery site. The method may further include heating the delivery cannula to a second temperature to actuate it to a second selected curvature before or after positioning the distal end distally adjacent the second region.

In still another aspect, presently disclosed embodiments may relate to a method of injecting curable material to a delivery site within a bone structure, where the method may include steps of providing a delivery cannula that includes an open proximal end, a distal segment opposite the proximal end having a distal tip, a lumen extending from the proximal end; locating a distal tip of a guide cannula within the bone structure; inserting the delivery cannula within the guide cannula; distally advancing the delivery cannula such that the distal end segment projects distal of the guide cannula distal tip, the distal end of the delivery cannula extending outside of a longitudinal axis substantially defined by the guide cannula; heating the delivery cannula to a first temperature to actuate it to a first selected curvature; manipulating the delivery cannula such that at least a portion of the distal segment creates one or more voids in soft body tissue within the bone structure; and delivering the curable material to the delivery site wherein the curable material is delivered to the one or more voids in the soft body tissue created by the distal segment. The method may further include heating the delivery cannula to a second temperature to actuate it to a second selected curvature, which may be used to create one or more further voids.

BRIEF DESCRIPTION OF THE DRAWINGS

The accompanying drawings are included to provide a further understanding of the present invention and are incorporated in and are a part of this specification. Other embodiments of the present invention, and many of the intended advantages of the present invention, will be readily appreciated as they become better understood by reference to the following detailed description. The elements of the drawings are not necessarily to scale relative to each other, nor do they necessarily accurately represent relative scale or proportions of embodiments depicted therein. Like reference numerals designate corresponding similar parts.

DETAILED DESCRIPTION

Figure 1:
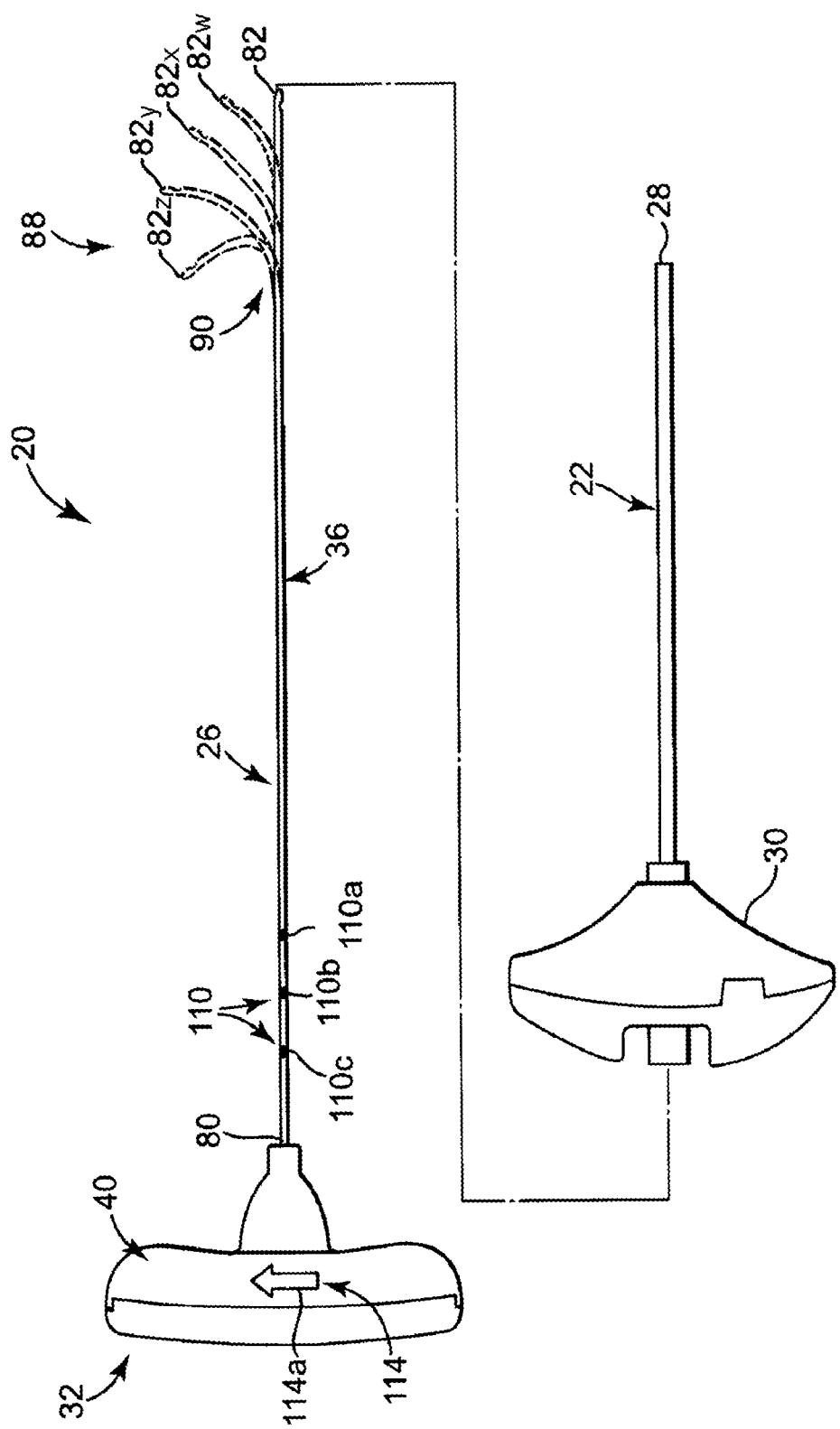
FIG. 1 illustrates components of an intraosseous curable material delivery system.

FIG. 1 illustrates components of an intraosseous, curable material delivery system 20. The system 20 includes an outer guide cannula 22 and a delivery cannula device 26 (referenced generally). Details on the various components are provided below. In general terms, however, a portion of the delivery cannula device 26 is sized to be slidably disposed within the guide cannula 22 that otherwise serves to form and/or locate a desired delivery site within bone. After it is positioned through the guide cannula lumen, the delivery cannula device 26 may be employed to inject a curable, bone stabilizing material into the delivery site. The system 20 can be used for a number of different procedures, including, for example, vertebroplasty and other bone augmentation procedures in which curable material is delivered to a site within bone, as well as to remove or aspirate material from a site within bone.

The system 20, and in particular the delivery cannula device 26, is highly useful for delivering a curable material in the form of a bone cement material. The phrase "curable material" within the context of the substance that can be delivered by the system/device of the invention described herein is intended to refer to materials (e.g., composites, polymers, and the like) that have a fluid or flowable state or phase and a hardened, solid or cured state or phase. Curable materials include, but are not limited to injectable polymethylmethacrylate (PMMA) bone cement, which has a flowable state wherein it can be delivered (e.g., injected) by a cannula to a site and subsequently cures into hardened cement. Other materials, such as calcium phosphates, bone in-growth material, antibiotics, proteins, etc., could be used in place of or to augment, PMMA (but do not affect an overriding characteristic of the resultant formulation having a flowable state and a hardened, solid or cured state). This would allow the body to reabsorb the cement or improve the clinical outcome based on the type of filler implant material. With this in mind, and in one embodiment, the system 20 further includes a source (not shown) of curable material fluidly coupled to the delivery cannula device 26.

Given the above, the outer guide cannula 22 generally enables access of the delivery cannula device 26 to a bone site of interest, and thus can assume a wide variety of forms. In general terms, however, the guide cannula 22 is sized to slidably receive a portion of the delivery cannula device 26, terminating in an open, distal tip 28. The distal tip 28 can further be adapted to facilitate coring of bone tissue, such as when using the guide cannula 22 to form a delivery site within bone. To promote a desired interface between the guide cannula 22 and a portion of the delivery cannula device 26 otherwise slidably inserted within the guide cannula 22 during use (described below), in one embodiment, an inner diameter surface of the guide cannula 22 is highly smoothed to a matte or mirror finish (i.e., RMS range of about 0-18). In another preferred embodiment, the inner diameter surface of the guide cannula 22 or the outer diameter surface of the delivery cannula 36 can be coated with, for example, polytetrafluoroethylene (PTFE) or another low-friction or lubricious material to promote a smooth desired interface between the guide cannula 22 and a portion of the delivery cannula device 26 otherwise slidably inserted within the guide cannula 22 during use. A PTFE sleeve between the guide cannula 22 and a portion of the delivery cannula device 26 may also be used. Further, the outer diameter surface of the delivery cannula 36 can be polished to a highly smoothed to a matte or mirror finish (i.e., RMS range of about 0-18). Regardless, and in some embodiments, the guide cannula 22 can further be attached, at a proximal end thereof, to a handle 30 for enhancing a surgeon's ability to manipulate the system 20. Alternatively, the handle 30 can be eliminated.

As shown in FIG. 1, the delivery cannula device 26 includes a memory metal material. The elongate tubular body 36, which may be embodied as a vertebroplasty needle or other bone augmentation needle, may be constructed of—for example—Nitinol and/or another memory metal. Memory-metal materials are well-known in the art. In certain embodiments, the body 36 may generally be formed as a polymeric tube with one or more lengthwise (linear, curved, spiral, etc.) memory metal supports. The memory metal supports may be disposed on one or more of an inner surface, an outer surface, and embedded in the wall of the polymeric tube (which may be, for example, made of PEEK or another suitable material with sufficient stiffness—as supported by the memory metal—to provide the structural and functional features described herein. As shown in FIG. 1, a cannula body 36 including a memory metal material may be configured to have a generally straight-line body at a first temperature, such as—for example—a typical ambient temperature, which body generally defines a longitudinal axis. In a polymeric tube body, the memory metal may provide both structural rigidity needed to operate in target tissue and the temperature-dependent curvature presently disclosed.

The memory metal portion of the body may be configured to provide at least a first curvature of a distal deflectable length of the cannula body 36 when heated to a first elevated temperature, a second curvature at a second elevated temperature, and so on for a plurality of temperature-dependent curvature states where the deflectable portion is curved out of the longitudinal axis by a known amount. This configuration of the memory metal (whether in tube form making up a significant body portion of the cannula, or as strut(s) or other structural elements) may be provided by thermosetting of the memory metal during manufacture, applying technology known and used in the art of memory metal manufacture.

By way of illustrative example, with reference to FIG. 1, at ambient temperature, the body 36 is generally straight, and—with reference to the following table—

| At about this temperature (e.g., +/−4° C.) | The curvature of the distal delivery cannula end 82 relative to the longitudinal axis may be about: | Corresponding to a dashed-line curved orientation in FIG. 1 designated by reference number: |
| --- | --- | --- |
| 45° C. | 30° | 82w |
| 55° C. | 60° | 82x |
| 65° C. | 90° | 82y |
| 75° C. | 120° | 82z |

These temperatures are examples only. Other curves corresponding to other temperatures may be included. Most preferably, the curvature desired may be assumed with a short application of heat to reach the desired temperature, where the heat and associated temperature are within relatively low-risk tolerances for a patient being treated. As another example, a temperature of about 60° C. may correspond to a curvature of about 45°, a temperature of about 70° C. may correspond to a curvature of about 90°, and a temperature of about 80° C. may correspond to a curvature of about 135°. In another embodiment, ambient temperature may correspond to a straight cannula, a temperature of about 65° C. may correspond to a curvature of about 55°, and a temperature of about 80° C. may correspond to a curvature of about 95°. In other words, subject to the physical limitations of the memory metal material, two, three, or more pre-set curves may be used that correspond with selected temperatures (where the greater degrees of curvature away from the longitudinal axis generally correspond to higher temperatures). The curves may range from more than 1, but less than about 10 degrees to nearly 180 degrees, with a preferred range of about 20 degrees to about 135 degrees.

During a vertebroplasty or other bone augmentation procedure, it may be desirable to access a location within the bone that is not readily accessible through a single-entry (e.g., unipedicular) approach using a straight needle or a delivery cannula available with a particular pre-set curve. Providing a plurality of delivery cannulas with different pre-set curvatures as part of a surgical kit presents barriers of cost and convenience not present in the present system. Additionally, the present system's cannula curvature may be adjusted "on the fly" by applying heat to the cannula sufficient to change the curvature. This may be useful if a physician, during a treatment procedure, wishes to access a different location within the target delivery site after a delivery cannula is already in place. A multi-needle system would require swapping out and reloading a new delivery cannula and most likely making a new batch of curable bone cement material. With the present system, a different curvature may be realized without incurring the additional time, expense, and risk associated with device exchange and extended procedural requirements.

Figure 2A:
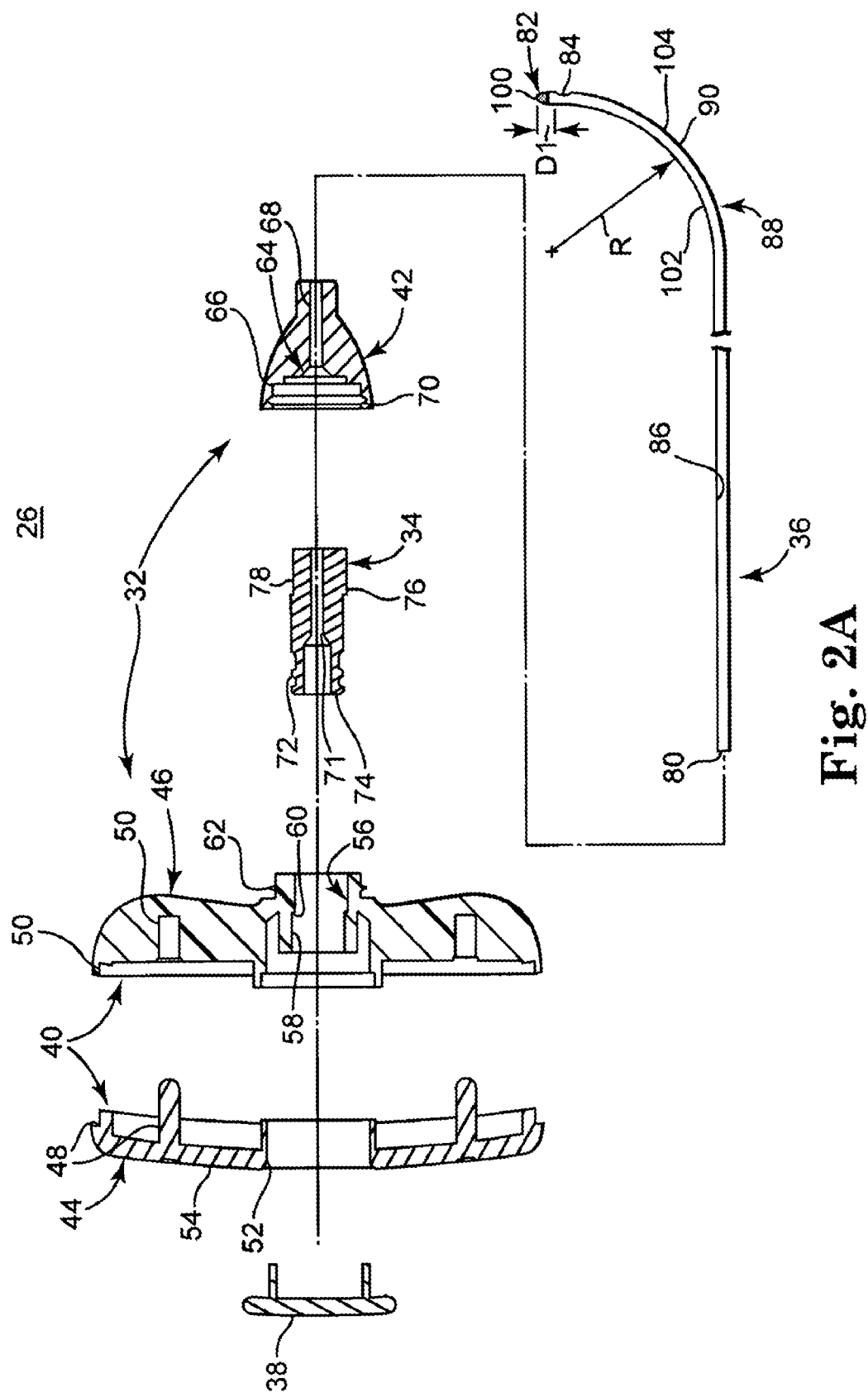
FIG. 2A is a cross-sectional, exploded view of a delivery cannula device component of the system of FIG. 1.

The delivery cannula device 26 is shown in greater detail in FIG. 2A, and generally includes a handle assembly 32 (referenced generally), a hub 34, and a delivery cannula 36. The hub port 34 forms a fluid port and is fluidly connected to the delivery cannula 36, with the handle assembly 32 retaining the combination hub 34/delivery cannula 36. As described in greater detail below, the delivery cannula 36 is sized to be coaxially, slidably received within the guide cannula 22 (FIG. 1), and is adapted to deliver a curable material injected therein via the hub 34.

The handle assembly 32 includes, in one embodiment, a handle 40 and a retainer 42. The handle 40 is adapted to receive the hub 34, with the retainer 42 securing the hub 34 (and thus the delivery cannula 36) to the handle 40.

The handle 40, in one embodiment, includes a first section 44 adapted for snap-fit assembly to a second section 46, such as by complimentary annular protrusion(s) 48 and grooves 50. Regardless, the first section 44 forms a central passage 52 extending inwardly from an exterior surface 54 thereof.

The second section 46 defines an internal aperture 56 that, upon final assembly of the handle 40, is aligned with the central passage 52. The aperture 56 can assume a variety of forms sized to receive the hub 34 in a nested manner. The nested interface between the handle 40 and the hub 34 is preferably adapted such that the hub 34 cannot rotate relative to the handle 40 upon final assembly (i.e., the hub 34/handle 40 interface resists a torque imparted on either component such that rotational movement of the handle 40 results in an identical rotation of the hub 34/delivery cannula 36 even when the delivery cannula 36 is inserted within a confined surgical site). Thus, in one embodiment, the aperture 56 and the hub element 34 (as described below) may have corresponding non-symmetrical or non-circular shapes in transverse cross-section. In one embodiment, the second section 46 may include exterior threads 62. Alternatively, the handle assembly 32 can assume a wide variety of other forms and in some embodiments can be eliminated entirely.

Figure 2B:
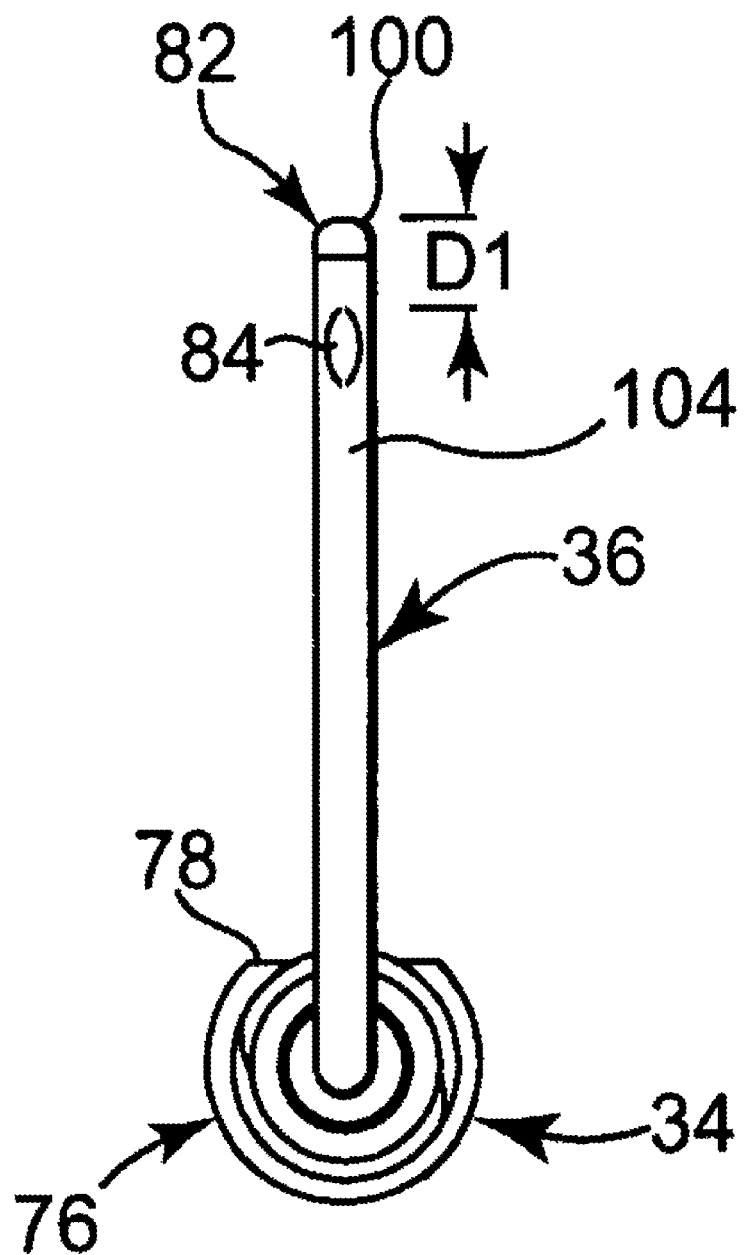
FIG. 2B is a front view of a delivery cannula and hub portions of the device of FIG. 2A.

In one embodiment, the hub 34 may include a conventional fluid port design and defines a fluid passage 71 and an exterior thread 72 on a proximal end 74 thereof. In one embodiment, the thread 72 is a double start right hand Luer thread including a 5-millimeter lead, although other thread conformations and lead sizes are also acceptable. Regardless, as previously mentioned, in one embodiment, the hub 34 is configured to be rotatably "locked" relative to the handle assembly 32 upon final assembly. Thus, in one embodiment, a body of the hub 34 forms a generally cylindrical surface 76 a portion of which is flattened in an area 78, as shown in FIG. 2B. The size and shape of the flattened area 78 corresponds with the aperture sidewall 58 (FIG. 2A) provided with the handle 40 (FIG. 2A). A removable cap 38 may be provided, adapted to attach to the first section 44 of the handle assembly 32 and cover the fluid passage 71 of the hub 34.

As shown in FIG. 2A, the delivery cannula 36 defines a proximal end 80 and a distal end 82, and forms one or more side orifices 84 adjacent the distal end 80 and in fluid communication with an internal delivery cannula lumen 86. In addition, the delivery cannula 36 includes a deflectable distal segment 88 (referenced generally) defining a plurality of pre-set curves or bends 90 as herein described. As described below, the deflectable segment 88, and in particular the bend(s) 90, includes or extends from the distal end 82, and has a shape memory attribute. As described above, and shown in FIG. 1, the deflectable segment 88 may be directed into different curvatures.

The proximal end 80 is axially open to the lumen 86. Conversely, the distal end 82 is axially closed to the lumen 86, and the distal end 82 defines or includes a blunt tip 100. For example, in one embodiment, the blunt tip 100 defines a hemispherical surface, although other blunt (i.e., curved or curvilinear) shapes or contours are also acceptable.

With reference to FIGS. 2A and 2B, the side orifice(s) 84 is formed adjacent the distal end 82, extending through a thickness of a sidewall of the delivery cannula 36. In one embodiment, a single orifice 84 is provided, and is located generally opposite a direction of the bend 90. In other words, relative to the longitudinal cross-sectional view of FIG. 2A, a direction of the bend 90 serves to form the delivery cannula 36 to define an interior bend side 102 and an exterior bend side 104. The side orifice 84 is formed along, and is open relative to, the exterior bend side 104.

Figure 3A:
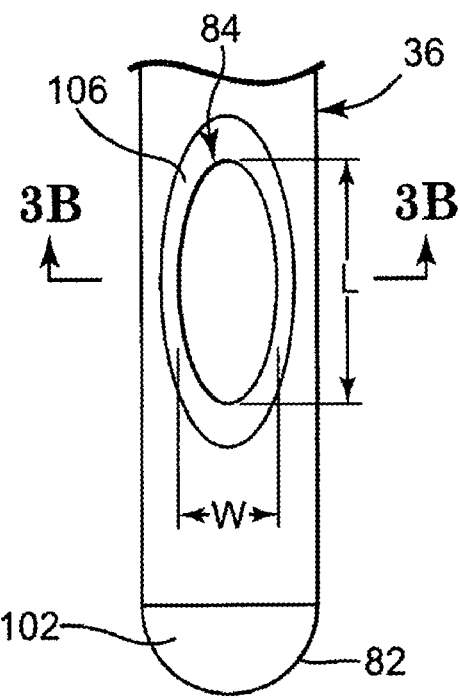
FIG. 3A is an enlarged plan view of a distal portion of the delivery cannula of FIG. 2A.

The side orifice(s) 84 can assume a wide variety of shapes and sizes (relative to an exterior surface of the delivery cannula 36). For example, the side orifice(s) 84 can be oval, circular, curvilinear, etc. In one embodiment, and with reference to FIG. 3A, a chamfered region 106 can be formed about the side orifice 84 to eliminate sharp edges along an exterior of the delivery catheter 36 as well as to promote consistent flow of curable material from the side orifice 84 (via the expanding orifice size effectuated by the chamfered region 106). With embodiments where the side orifice 84 is non-circular, an orifice length L and width W are defined. To this end, the length L may be greater than 0.050 inch, preferably greater than 0.075 inch, and even more preferably greater than 0.100 inch. The side orifice 84 may be characterized as being relatively large, especially as compared to conventional bone cement delivery needles that otherwise provide only an axial orifice or opening at the distal tip.

Figure 3B:
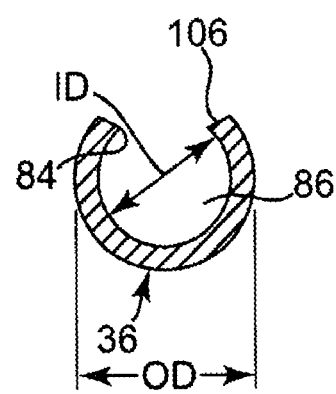
FIG. 3B is a cross-sectional view of the delivery cannula of FIG. 3A.

In particular, and with additional reference to FIG. 3B (otherwise illustrating a cross-sectional view of the delivery cannula 36 taken through the side orifice 84), the delivery cannula 36 defines an inside diameter ID (i.e., a diameter of the lumen 86). The side orifice 84 is fluidly connected to the lumen 86 and extends in a radial fashion. With these conventions in mind, in one embodiment, the length L of the side orifice 84 is greater the inside diameter ID of the delivery cannula 36. As such, at least one linear dimension of the side orifice 84 is larger than any orifice dimension that could otherwise be achieved were an orifice to be formed at the distal end 82 (i.e., an axially extending orifice). That is to say, an orifice formed at and by the distal end 82 of the delivery cannula 82 (as is conventionally employed in the bone cement delivery needle art) is limited in size (i.e., diameter) by the inside diameter ID of the delivery cannula 36. In contrast, the side orifice 84 in accordance with principles of the present invention is much larger, presenting a distinct advantage when attempting to pass a high viscosity liquid (curable material such as bone cement) therethrough.

Figure 4:
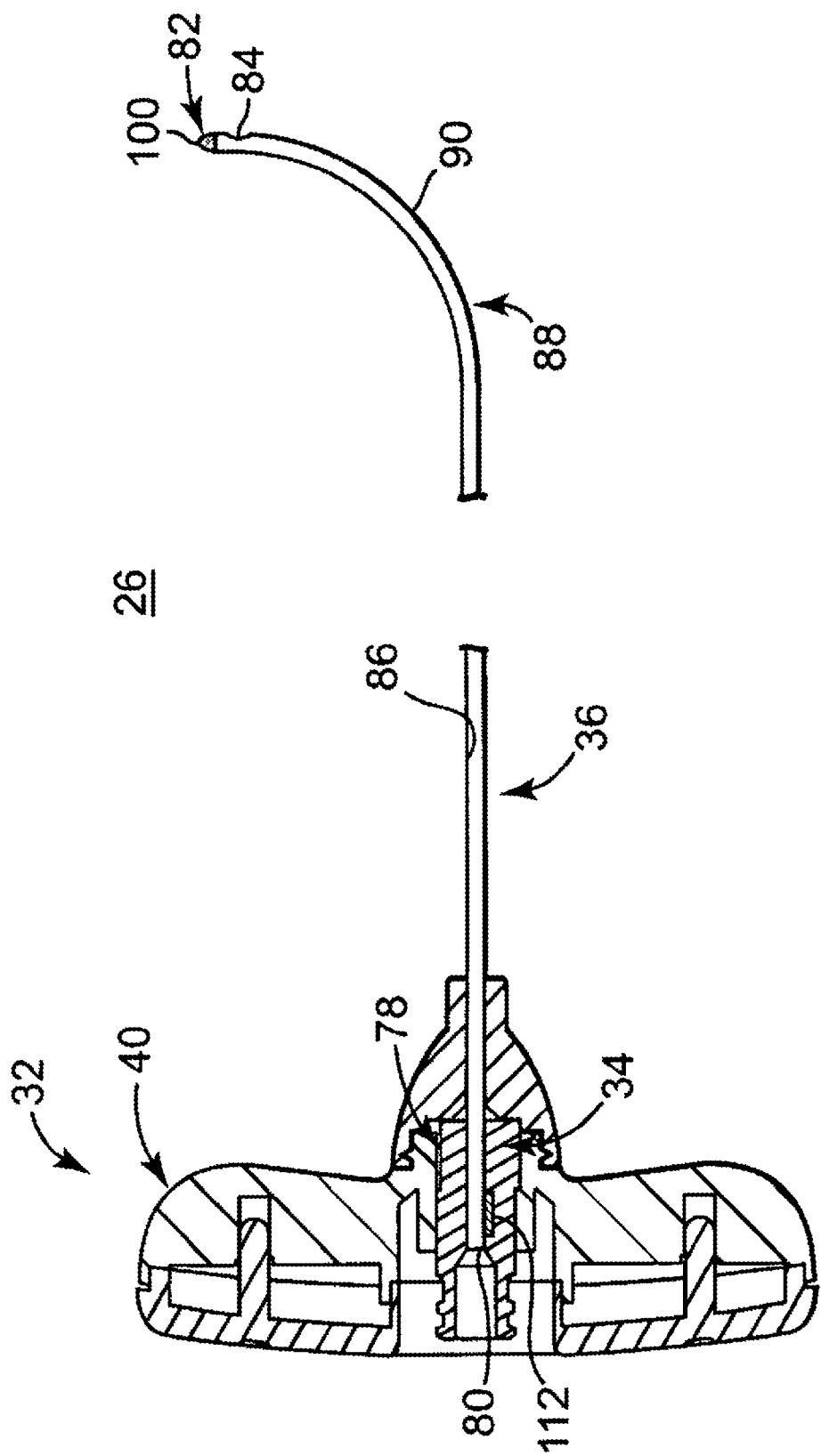
FIG. 4 is a cross-sectional view of the delivery cannula device of FIG. 2A upon final assembly.

Returning to FIG. 2A, in one embodiment, the delivery cannula 36 defines a continuous length between its proximal end 80 and its distal end 82, with its deflectable segment 88 including the bend 90, extending along approximately 25% of the length from the distal end 82 (where the length of the delivery cannula 36 is the length of extension from the hub 34 upon final assembly). In other embodiments suited for other surgical procedures, the deflectable segment 88, and in particular the bend 90, may extend along between 10%-50% of the length of the delivery cannula 36 as measured from the distal end 82. FIG. 4 shows an assembled view of the delivery cannula device 26 that was shown in exploded longitudinal section view of FIG. 2A.

To facilitate delivery of a curable material (e.g., bone cement) into a confined site within bone (such as with a vertebroplasty procedure), the deflectable segment 88 can be formed to define the bend 90 at a radius of curvature R, with the distal tip 100 offset from the longitudinal axis of the body 36 at a predetermined angle desired for targeting delivery to a particular site.

Further, to facilitate ready deflection of the deflectable segment 88 from the curved shape to a substantially straightened state (such as when the delivery cannula 36 is inserted within the outer guide cannula 22 (FIG. 1)) and reversion back to the curved shape, the delivery cannula 36, or at least the deflectable segment 88, is formed of a shape memory metal. In one embodiment, the delivery cannula 36 comprises Nitinol™, a known shape memory alloy of nickel (Ni) and titanium (Ti). In one embodiment, the bend 90 is formed in the delivery cannula 36 by deforming a straight fluid delivery cannula under extreme heat for a prescribed period of time, which pre-sets a curved shape in the delivery cannula 36.

In another embodiment, the pre-set curve or bend 90 is formed in an initially straight cannula by cold working the straight cannula and applying a mechanical stress. Cold working permanently locks a crystalline structure (for example, at least a partial martensitic crystalline structure) in a portion (i.e., the deflectable segment 88) of the cannula, while an unstressed portion remains in, for example, an austenitic structure.

In addition to Nitinol, other materials exhibiting this shape memory behavior can be employed, including superelastic or pseudoelastic copper alloys, such as alloys of copper, aluminum, and nickel, and alloys of copper, aluminum, and zinc, and alloys of copper and zinc. Regardless, the deflectable segment 88 is formed to be resilient and to assume the desired radius of curvature R under pre-determined conditions, as defined. In this manner, after the delivery cannula 36, and in particular the deflectable segment 88, is oriented a substantially straightened shape at a typical ambient temperature (as shown in FIG. 1), upon being heated, the deflectable segment 88 "remembers" the pre-set curved shape(s) and reversibly relaxes/returns to a first, second, or further curvature defining a bend 90, as described in detail below.

An additional feature of the delivery cannula 36 in accordance with one embodiment is shown in the plan view of FIG. 1, which includes indicia 110 (referenced generally) adjacent the proximal end 80. The indicia 110 are indicative of a location of the distal end 82 relative to the distal tip 28 of the guide cannula 22 upon insertion of the delivery cannula 36 within the guide cannula 22. For example, the indicia 110 may include first, second, and third depth markings 110a, 110b, 110c corresponding to a set distance of extension from the distal end of the guide cannula. That is, a longitudinal location of the first depth marking 110a relative to the distal end 82 (when the delivery cannula 36 is in a generally or substantially straightened state) may be commensurate with a length of the guide cannula 22 in combination with the handle 30 (where provided).

In another preferred embodiment, the present invention includes a probe (not shown) in the form of a wire that can be inserted into the delivery cannula device 26 to remove blockages that may form within the delivery cannula 36. Preferably, the probe has a diameter that is smaller than the inner diameter of the delivery cannula 36 to allow material within the delivery cannula 36 to flow around the probe as the probe is inserted into the delivery cannula 36. In one preferred embodiment, the probe is flexible enough to travel through the curvature of the delivery cannula 36, but still rigid enough to remove blockages within the delivery cannula 36.

Figure 5:
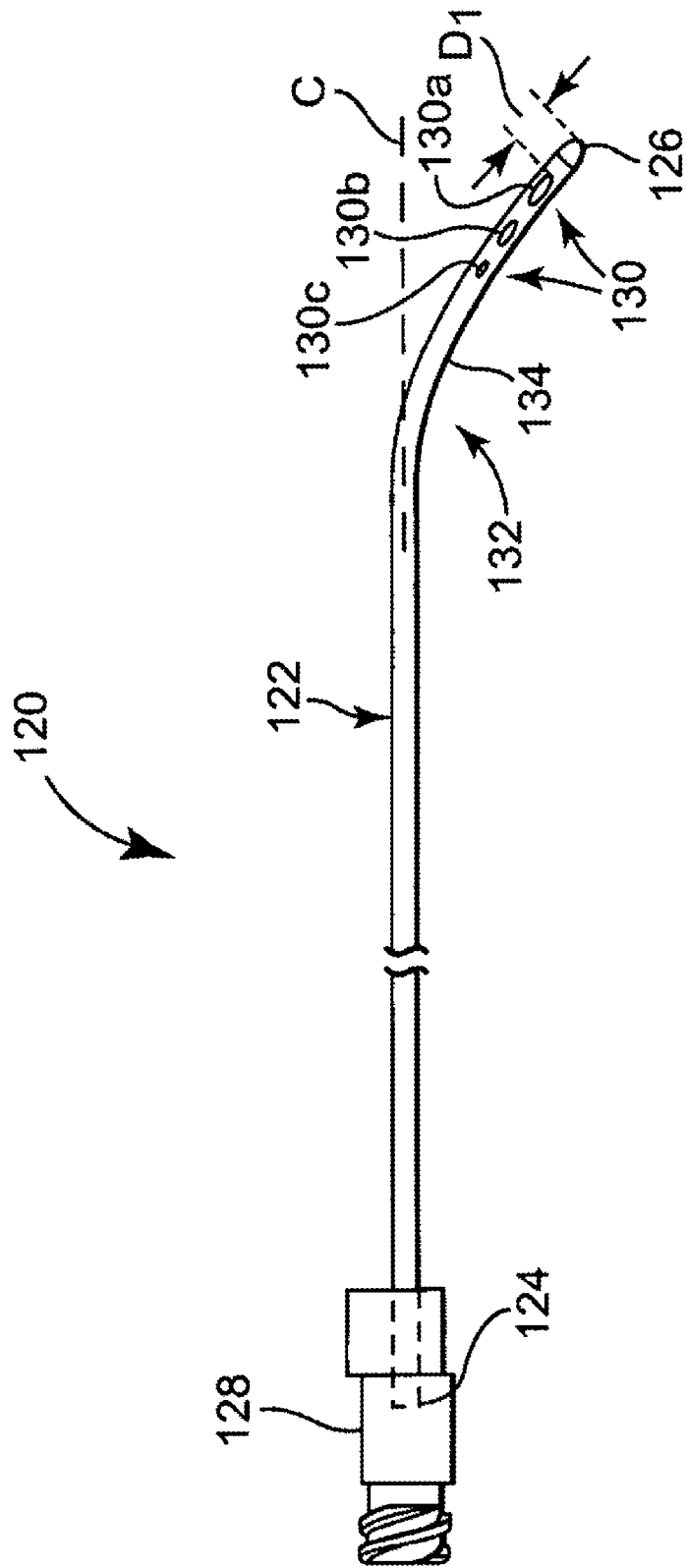
FIG. 5 is a side plan view of another embodiment of a delivery cannula device.

Although the delivery cannula device 26 has been described as including the delivery cannula 36 otherwise forming one side orifice 84, a variety of other configurations are also acceptable. For example, two or more circumferentially aligned side orifices can be provided. Further, FIG. 5 illustrates portions of a different embodiment delivery cannula device 120. The delivery cannula device 120 includes a delivery cannula 122 that extends a length between a proximal end 124 and a distal end 126, and a hub 128 coupled to the proximal end 124. The delivery cannula 122 is similar to the delivery cannula 36 (FIG. 2A) described above (including a blunt tip), but forms a series of longitudinally aligned side orifices 130, spaced along a length of the delivery cannula 122, and fluidly connected to an internal lumen (not shown). Further, the delivery cannula 122 includes a deflectable segment 132 forming a plurality of pre-set temperature-dependent curves along a segment 134, similar to previous embodiments (only one of which is shown in FIG. 5).

A distal-most side orifice 130a is offset a distance D1 from the distal end 116. Once again, the distance D1 is, in one embodiment, in the range of 0.05-0.5 inch, preferably in the range of 0.1-0.25 inch. A longitudinal spacing between the remaining side orifices 130 proximal the distal-most side orifice 130a can vary. Preferably, however, the second side orifice 130b defines a smaller sized opening as compared to the distal-most side orifice 130a, and the third side orifice 130c is smaller than the second side orifice 130b. This reduction in side orifice size proximal the distal end 126 promotes consistent distribution of curable material otherwise being forced through the delivery cannula 122.

While three of the side orifices 130 are shown, other configurations are also acceptable. For example, multiple side orifices (i.e., two or more than three side orifices) can be formed longitudinally along the length of the delivery cannula 122, and in addition, the side orifices 130 can include more than one longitudinally aligned series of side orifices. In an exemplary embodiment, the side orifices 130 that are visible in FIG. 5 are matched by another column of longitudinally aligned side orifices formed on an opposing side of the delivery cannula 122 (and therefore not visible in the view of FIG. 5). Aspects of the present invention provide for the side orifices 130 to define circular side orifices, non-circular side orifices, or a set of circular and non-circular side orifices.

As a point of reference, the pre-set curve 134 shown is curved away from a central longitudinal axis C of the delivery cannula 122 such that the curvature of the pre-set curve 134 is less than the radius of curvature R of the pre-set curve 90 (FIG. 2A) previously described, thus illustrating another embodiment in accordance with principles of the present invention. In addition, while the side orifices 130 are depicted as formed along the pre-set curve 134, in another embodiment at least one of the side orifices 130 may be formed proximal the pre-set curve 134.

Figure 6A:
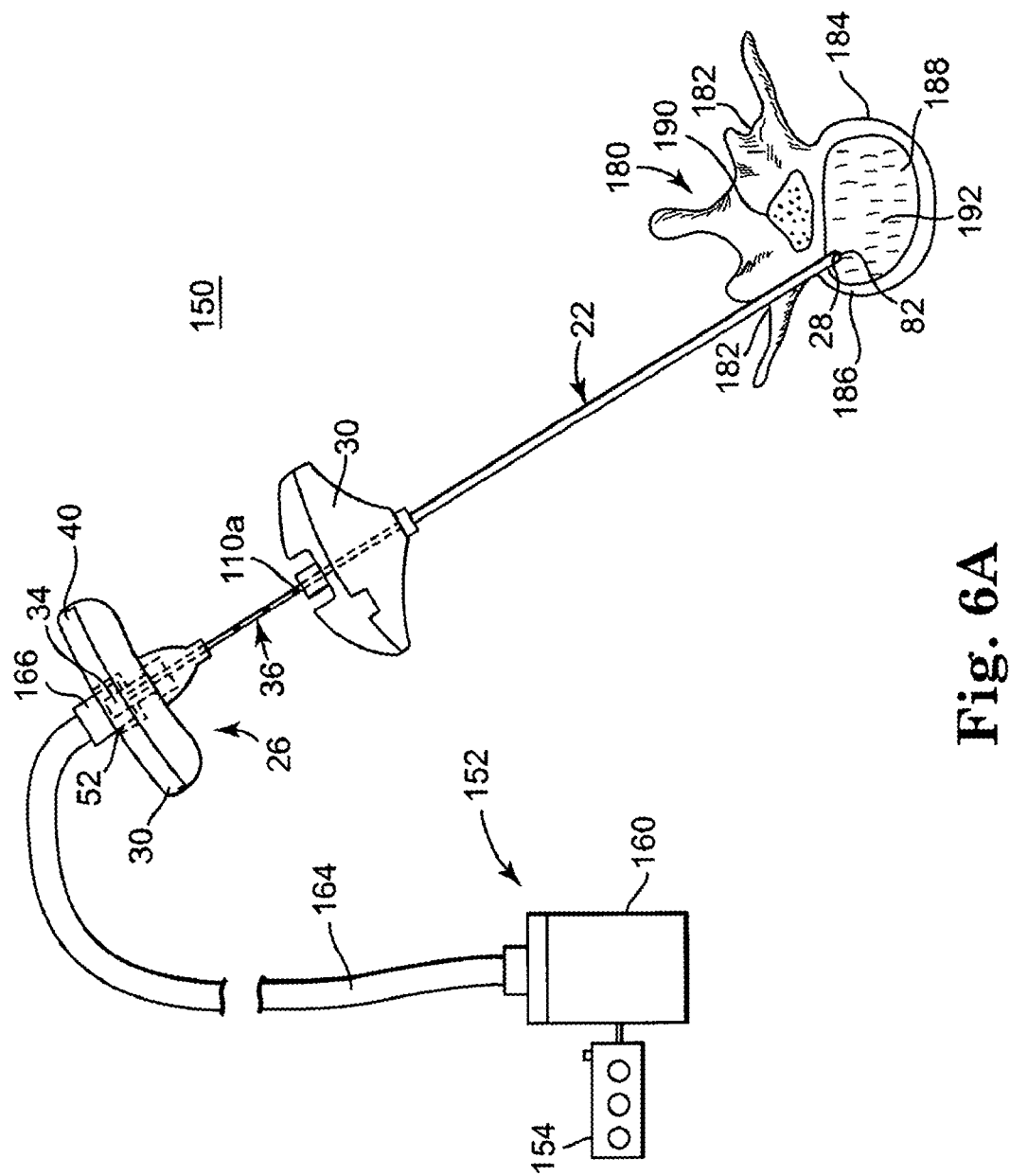
FIG. 6A is a simplified plan view of an intraosseous curable material delivery system employed in a palliative bone procedure.

Regardless of an exact configuration, the assembled delivery cannula device (such as the delivery cannula device 26 of FIG. 4) in accordance with principles of the present invention is highly useful in performing a wide variety of bone stabilizing procedures as part of an overall curable material delivery system. To this end, FIG. 6A illustrates an intraosseous curable material delivery system 150 according to one embodiment of the present invention, employed to perform a vertebroplasty procedure. The system 150 includes the outer guide cannula 22, the delivery cannula device 26, a curable material source 152 fluidly coupled to the delivery cannula device 26, and a controller 154 coupled to at least the curable material source 152.

The curable material source 152 includes, in one embodiment, a canister 160 containing a curable material as previously described, and tubing 164 extending from the canister 160 to the handle assembly 30 of the delivery cannula device 26. In this regard, the tubing 164 terminates at a fitting 166 configured to removably attach to the hub 34. In particular, the fitting 166 is configured to fit within the passage 52 of the handle 40 and removably couple to the hub 34. In one embodiment, the fitting 166 threads onto a Luer thread defined by the hub 34. In another embodiment, the fitting 166 snap-fits over the hub 34. Alternatively, a wide variety of other attachment configurations are also available.

The controller 154 can assume any form known in the art and may be coupled to a curable material source 152. In one example of an embodiment, the controller 154 will control a mass flow and a mass flow rate (i.e., a fluid delivery rate) of curable material from the canister 160 to the delivery cannula device 26, as well as a temperature of the delivery cannula (by providing heat energy calibrated and controlled to generate a specific desired temperature corresponding to a desired pre-set curvature). The heat energy may be provided by any number of means known in the art including—by way of illustrative example—resistance circuits, RF energy, injection through the cannula of heated water or other material, ultrasonic energy, or other means. The controller 154 can include a variety of actuators (e.g., switch(es), foot pedal(s), etc.) affording a user the ability to remotely control liquid flow into the delivery cannula 36 and/or to control temperature (with the latter actuator(s) preferably including indicia corresponding to the temperature and/or curvature desired). Alternatively, manual control can be employed such that the controller 154 can be eliminated for use in dispensing curable material.

As shown in FIG. 6A, during a palliative bone procedure such as a bone augmentation procedure (shown here as a vertebroplasty), with the delivery cannula 36 partially retracted within, or entirely removed from, the outer guide cannula 22, the outer guide cannula 22 is located at a desired delivery site within bone. For example, in a vertebroplasty procedure the outer guide cannula 22 is introduced into a vertebra 180, preferably at a pedicle 182. In this regard, the vertebra 180 includes a vertebral body 184 defining a vertebral wall 186 surrounding bodily material (e.g., cancellous bone, blood, marrow, and other soft tissue) 188. The pedicle 182 extends from the vertebral body 184 and surrounds a vertebral foramen 190. In particular, the pedicle 182 is attached posteriorly to the vertebral body 184 and together they comprise the vertebrae 180 and form the walls of the vertebral foramen 190. As a point of reference, the intraosseous system 150 is suitable for accessing a variety of bone sites. Thus, while a vertebra 180 is illustrated, it is to be understood that other bone sites can be accessed by the system 150 (i.e., femur, long bones, ribs, sacrum, etc.).

The outer guide cannula 22 forms an access path to a delivery site 192 (or forms the delivery site 192) through the pedicle 182 into the bodily material 188. Thus, as illustrated, the outer guide cannula 22 has been driven through the pedicle 182 via a transpedicular approach. The transpedicular approach locates the outer guide cannula 22 between the mammillary process and the accessory process of the pedicle 182. In this manner, the outer guide cannula 22 provides access to the delivery site 192 at the open, distal tip 28. With other procedures, the outer guide cannula 22 can similarly perform a coring-like operation, forming an enlarged opening within bone. In one preferred embodiment illustrated in FIG. 6A, the distal tip 28 of the guide cannula 22 is positioned close to the entrance point into the delivery site 192. As will be explained in more detail herein, the smaller the projection of the distal tip 28 into the delivery site 192 allows for greater access for the delivery cannula 36 to be positioned within the delivery site 192 and deliver curable material to desired locations within the delivery site 192.

After the outer guide cannula 22 has formed, or is otherwise positioned within bone at, the desired delivery site 192, the delivery cannula 36 is slidably inserted/distally advanced within the outer guide cannula 22. It should be appreciated that a stylet, drill, or other instrument may be used as known in the art to form a delivery site 192 (e.g., directed through the guide cannula 22, used to form the site, then withdrawn before insertion of the delivery cannula). As illustrated generally in FIG. 6A, the distal end 82 of the delivery cannula 36 is poised at the distal tip 28 of the outer guide cannula 22. Approximate alignment of the first depth marking 110a with the handle 30 provides a user with visual confirmation (at a point outside of the patient) of the distal end 82 positioning relative to the outer guide cannula 22 distal tip 28. Prior to further distal movement, the delivery cannula 36 is entirely within the outer guide cannula 22 with the deflectable segment 88 (FIG. 2A) of the delivery cannula 36 in a substantially straightened shape that generally conforms to a shape of the outer guide cannula 22.

Figure 6B:
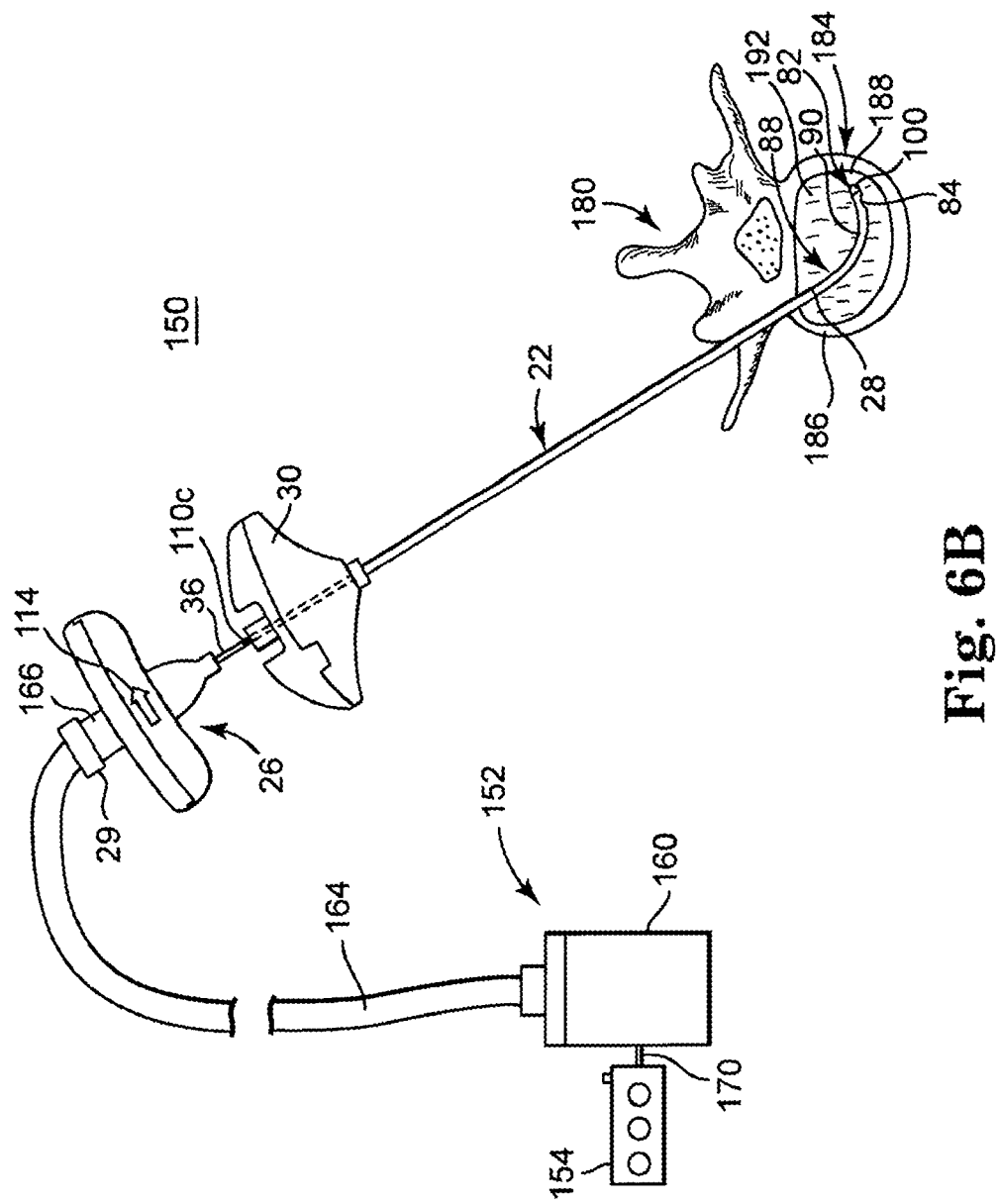
FIG. 6B illustrates a stage of a procedure performed by the system of FIG. 6A.

The delivery cannula device 26, and in particular the delivery cannula 36, is then distally advanced within the guide cannula 22 as shown in FIG. 6B. In particular, the delivery cannula 36 is distally maneuvered such that at least a portion of the deflectable segment 88 extends beyond the open tip 28 of the guide cannula 22 and into the delivery site 192. The deflectable segment 88 may be actuated to deflect to a desired pre-set first, second, or other curvature upon exiting the guide catheter 22, assuming the pre-set curvature of the bend 90 described above due to the shape memory characteristic being activated by application of heat energy to heat the needle to a corresponding temperature as described above. The user can visually confirm a length of distal extension of the delivery catheter 36 from the guide catheter 22 via a longitudinal positioning of the indicia 110b or 110c (the indicia 110c being visible in FIG. 6B) relative to the handle 30. Further, the directional indicia 114 indicate to a user (at a point outside of the patient) a spatial direction of the bend 90 that may be assumed within the delivery site 192 relative to a spatial position of the handle 40.

The blunt tip 100 of the distal end 82 is hemispherically shaped (or other non-sharpened or blunt shape) and thus atraumatic relative to contacted tissue/bone. As such, the blunt tip 100 can contact and/or probe the vertebral wall 186 with a minimum of risk in puncturing or coring the vertebral body 184. Thus, the blunt tip 100 offers an advantage over the conventional, sharp-edged bone cement delivery needles. The side orifice 84 is offset from the distal end 82 and is, therefore, available to deliver curable material into, and remove bodily material from, the delivery site 192. In particular, the side orifice 84 can eject curable material radially from, and aspirate bodily material into, the delivery cannula 36, even when the distal end 82 is pressed against a surface, such as an interior wall of the vertebral body 184.

Figure 6C:
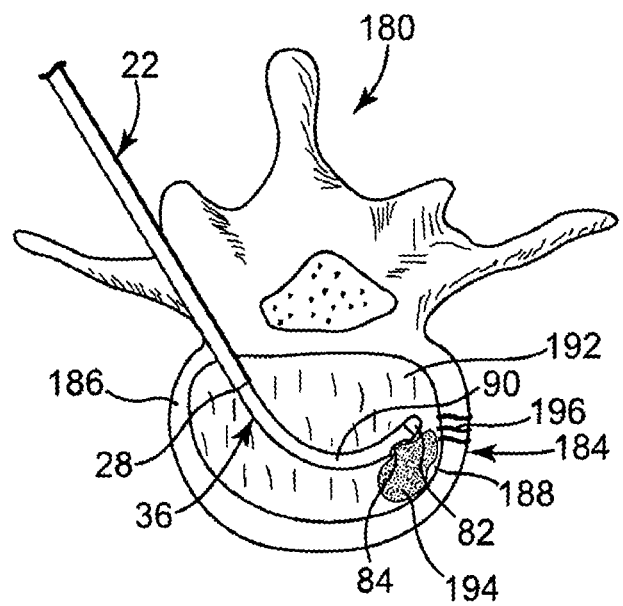
FIG. 6C is a transverse, sectional view of a vertebral body in combination with a portion of the system of FIG. 6A, illustrating injection of curable material after the delivery cannula has been curved by application of heat thereto to reach a temperature corresponding to a desired curve.
Figure 6D:
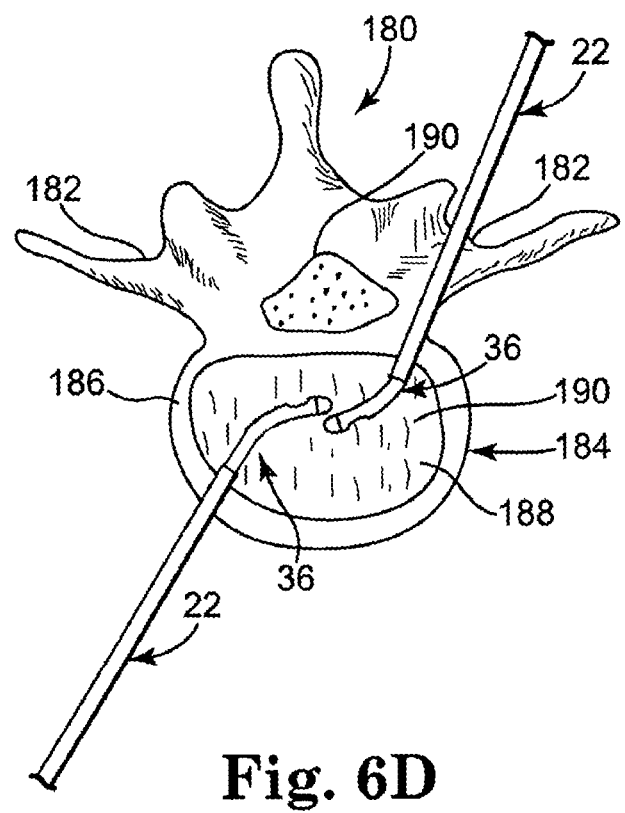
FIG. 6D is a transverse, sectional view of a vertebral body illustrating possible vertebroplasty approach positions using embodiments disclosed herein.
Figure 7A:
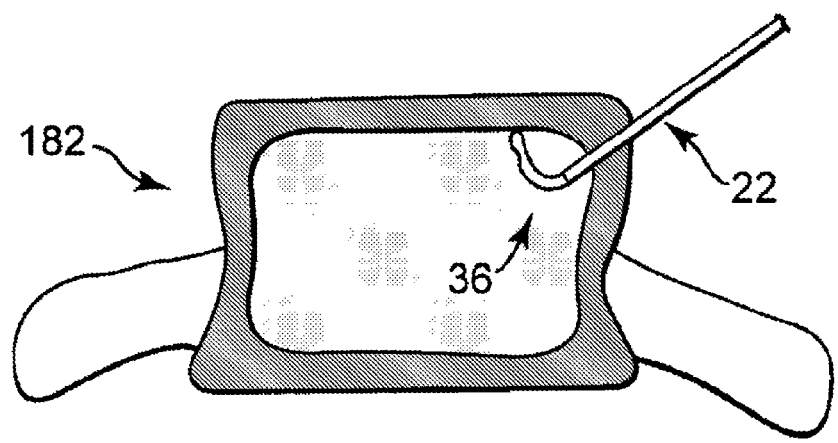
FIGS. 7A-7C are simplified anterior views of a vertebral body, illustrating use of one device embodiment.
Figure 7B:
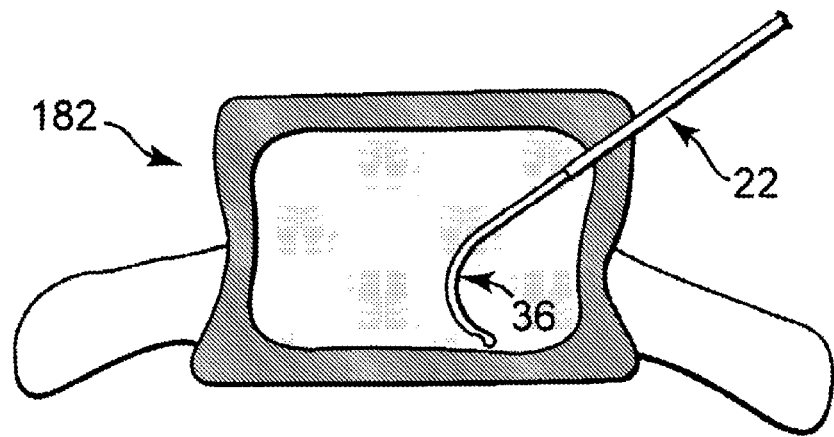
Figure 7C:
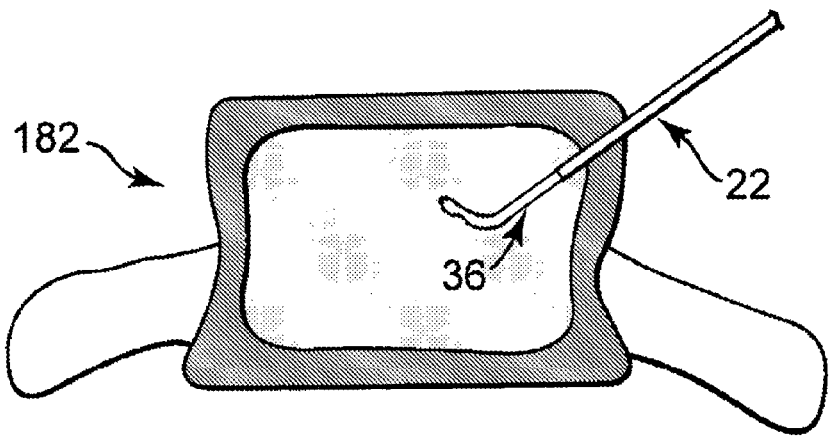

With the above in mind, in one embodiment, the fluid source 152 may then be operated (e.g., via the controller 154) to deliver a curable material (not shown) to the delivery cannula 36 via the hub 34. Curable material entering the delivery cannula 36 is forced through the lumen 86 (FIG. 2A) towards the side orifice 84. As shown in FIG. 6D, the curable material is then dispensed/injected from the delivery cannula 36 in a radial fashion from the side orifice(s) 84 and into the delivery site 192 in a cloud-like pattern 194. Alternatively or in addition, the delivery site 192 can be aspirated by replacing the curable material source 152 (FIG. 6A) with a vacuum source (not shown).

In another embodiment, curable material is preloaded in the delivery cannula. That is, the curable material delivered to the delivery cannula 36 before introducing the delivery cannula 36 into the guide cannula 22. In practice, an operator may advance curable material beyond the side orifice(s) 84 the delivery cannula 36 in order to completely fill the delivery cannula 36 and then wipe the side orifice(s) 84 of excess curable material before insertion into the guide cannula 22. The delivery cannula 36 is thus preloaded with curable material before the delivery cannula 36 is connected with the guide cannula 22. After the delivery cannula 36 is inserted into the guide cannula 22 curable material is immediately available to be delivered into the implantation site. This preloading step advantageously reduces the time required to deliver curable material into a patient because it can be done at substantially the same time the guide cannula 22 has being driven into the delivery site.

Importantly, by injecting the curable material radially from a side of the delivery cannula 36 rather than axially from the distal most end (as will otherwise occur with conventional delivery needles), the system 150 (FIG. 6A) can avoid forcing the curable material into a fracture or other defect that may in turn lead to undesirable leaking of the curable material through the fracture. By way of example, FIG. 6C illustrates a fracture 196 in the vertebral body wall 186. Vertebroplasty is a common solution to such vertebral fractures, with the accepted repair technique entailing positioning the distal end 82 at or "facing" the fracture 196 to ensure that the curable material is dispensed in relatively close proximity thereto. With known delivery needles, this preferred approach results in the curable material being injected directly toward the fracture 196. In contrast, with the delivery catheter 36 of the present invention, the distal end 82 is still "facing" or at least very near the fracture 196, yet the injected curable material cloud 194 is not forced directly toward the fracture 196. Instead, the curable material cloud 194 indirectly reaches the fracture 196 with minimal retained propulsion force such that the curable material cloud 194 is unlikely to forcibly leak through the fracture 196. However, the delivery site 192 is, as a whole, still filled with the curable material cloud 194 to effectuate the desired repair.

As shown in FIG. 6C, an entirety of the delivery site 192 is accessible by the delivery cannula 36. To this end, while the guide cannula 22 has been inserted via a right posterior-lateral approach, the system 150 can effectuate a vertebroplasty procedure from a left posterior lateral approach, or to right or left anterior lateral approaches as shown in FIG. 6D (which shows two approaches, that could be used together, or in the alternative).

Figure 8A:
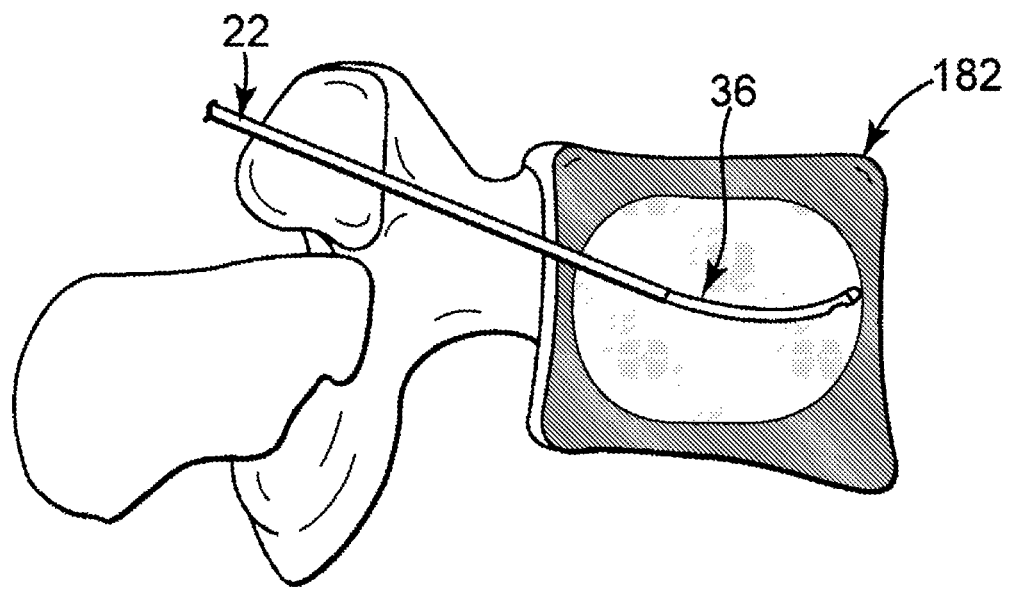
FIGS. 8A and 8B are simplified lateral views of a vertebral body, illustrating use of one device embodiment.
Figure 8B:
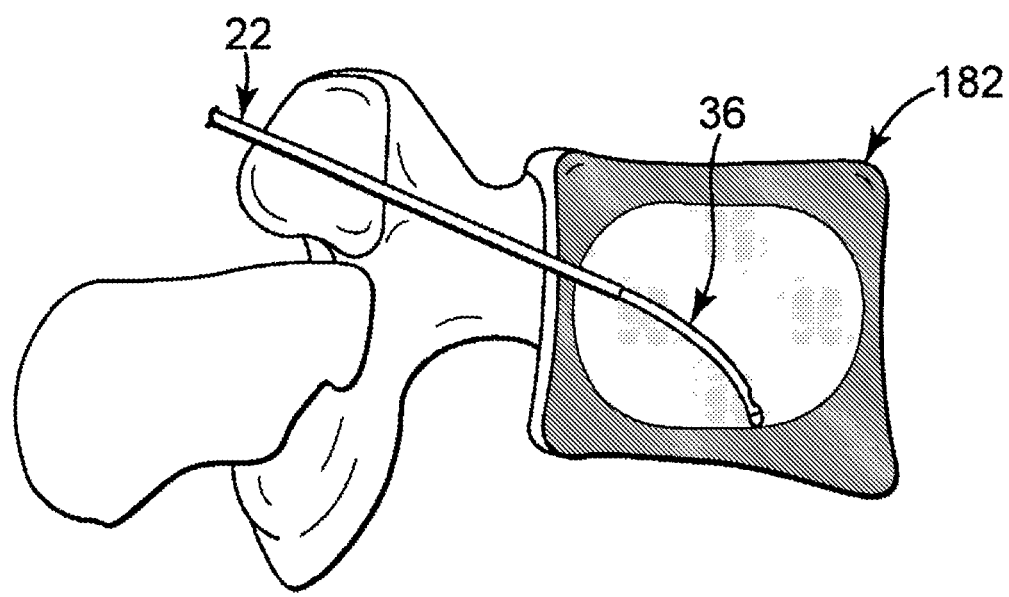

In more general terms, during the palliative bone procedure, a clinician operating the intraosseous system 150 extends the deflectable end length of the cannula body 36 into the delivery site 192 otherwise defined within bone. In one embodiment, a subsequent rotation of the delivery cannula 36 rotates a spatial position of the side orifice 84 relative to the delivery site 192, thus accessing multiple planes of the delivery site 192 with only one "stick" of the outer guide cannula 22. Thus, by a combination of retracting the delivery cannula 36 within the outer guide cannula 22, distally advancing the delivery cannula 36 relative to the outer guide cannula 22, by rotating the delivery cannula 36, and by actuating the cannula to a different curvature by providing the corresponding heat/temperature, multiple planes and multiple regions of the bone site of interest can be accessed by the delivery cannula 36 with a single approach of the outer guide cannula 22. Thus, for example, a unipedicular vertebroplasty can be accomplished with the system 150. FIGS. 7A-8B generally illustrate (FIGS. 7A-7C from an anterior perspective using three different curvatures; FIGS. 8A and 8B from a left lateral perspective) various planes/regions of the vertebral body 182 accessible with rotation and/or advancement of the delivery cannula 36 relative to the guide cannula 22, including with changing curvatures (again with the guide cannula 22 remaining stationary). Notably, in the drawings of FIGS. 7A-8B, a direction of the bend defined by the delivery cannula 36 is not necessarily perpendicular to the plane of the page, such that the bend may not be fully evident in each view.

Figure 9:
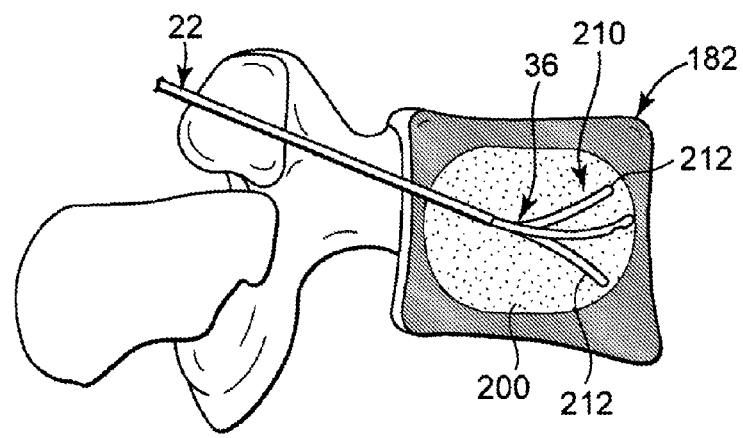
FIG. 9 is a simplified lateral view of a vertebral body, illustrating use of one device embodiment.
Figure 10:
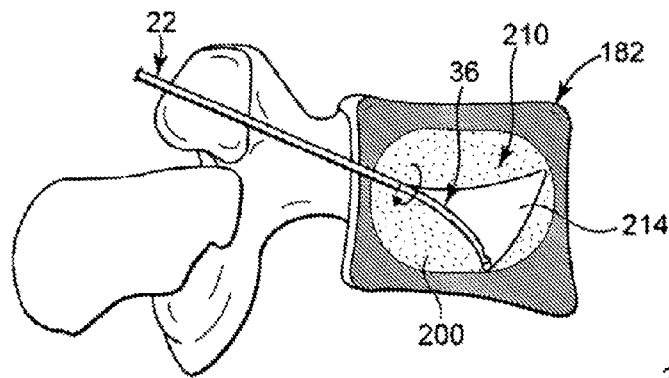
FIGS. 10-10A show a simplified lateral view of a vertebral body, illustrating use of one device embodiment.

With reference to FIGS. 9-10, another preferred method for delivering curable material is depicted. In this preferred embodiment, a clinician creates voids 210 in soft body material 200 (e.g., cancellous bone, blood, marrow, and other soft tissue) within a bone delivery site by manipulating the curved end 90 of the delivery cannula 36. The voids 210 can then be filled with curable material. It has been observed that when voids are created, curable material delivered to the delivery site will generally flow into the voids 210 instead of the soft body material 200. As a result, a clinician can create a void 210 at a relatively small desired area, and fill primarily just that area with curable material.

According to one preferred embodiment, voids can be created through a combination of retracting the delivery cannula 36 within the outer guide cannula 22 and distally advancing the delivery cannula 36 relative to the outer guide cannula 22, thus moving the curved end 90 in a reciprocating manner. The reciprocating action causes the curved end 90 to crush the soft body tissue and create a channel 212 within the soft body material. Additionally, by retracting the delivery cannula 36 within the outer guide cannula 22 and rotating the delivery cannula 36 so that the curved end 90 will distally advance within the delivery site at a different orientation, the curved end 90 can create multiple channels 212 within the soft body tissue 200. Further, the curved end 90 of delivery cannula 36 may be advanced distally only partially within the delivery site and then removed to create shorter channels 212 within the implantation site where desired. Actuating the different curvatures of the presently-disclosed delivery cannula may enable formation of a greater variety and/or number of voids than previously available via a single guide cannula without the disadvantages associated with exchanging out a delivery cannula for one with a different needed curvature, or having to settle for a different injection site than desired.

Figure 10A:
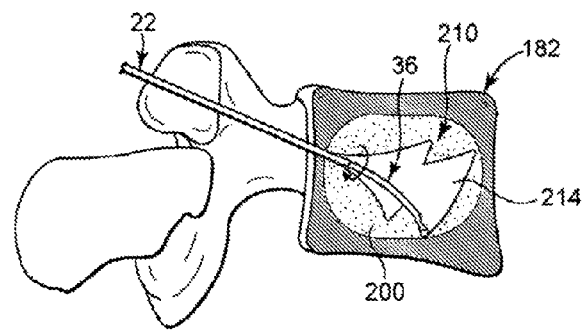

According another preferred embodiment shown in FIG. 10, the delivery cannula 36 can be rotated or spun after the curved end 90 has been introduced into the implantation site. The rotating or spinning of the delivery cannula 36 causes the curved end 90 to rotate through body tissue 200 to create a cone-shaped void 214 in the soft tissue 200 within the delivery site. As shown in FIG. 10A cone-shaped voids 214 of different sizes and locations may be created by inserting the curved end 90 into the implantation site by less than its full length and/or at different actuated curvatures and, thereafter, rotating the delivery cannula 36. If it is desirable to insert the delivery cannula 36 through the guide cannula by less than its full length, it may be advantageous to use one or more spacers such as those disclosed in U.S. Pat. No. 8,128,633, which is incorporated herein by reference in its entirety.

Voids 210 within the soft body tissue of various sizes and shapes can be created by using a combination of the above disclosed methods. According to one preferred method, a physician may introduce curable material within the implantation site as he or she is creating the voids within the implantation site. Thus, the voids may be created and filled at the same time. One skilled in the art will appreciate that whether voids are first created and then filled, or curable material may be delivered in a cloud-like pattern through the existing intravertebral tissue without first creating voids, the delivery cannula of the present invention can be manipulated to deliver small deposits of curable material to specific desired areas within a cavity.

Figure 11A:
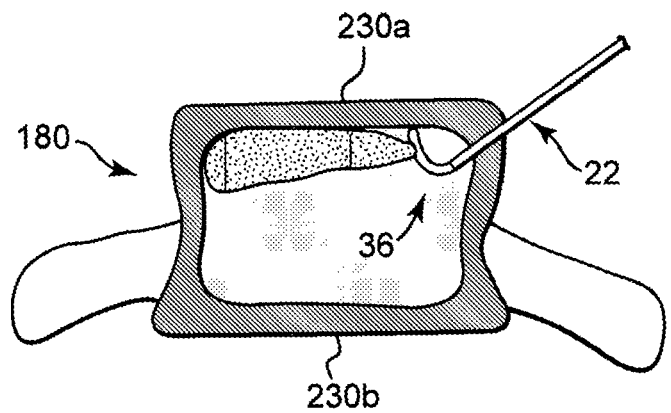
FIGS. 11A-11C are simplified anterior views of a vertebral body, illustrating use of one device embodiment.
Figure 11B:
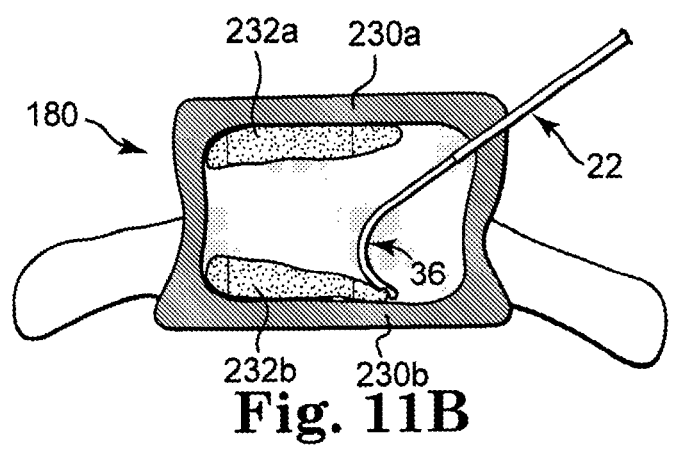

In one embodiment, curable material can be delivered in different planes to form curable material structures within the cavity to stabilize the endplates of a vertebral body 180, as depicted in vertical transverse section in FIGS. 11A and 11B. The vertebral body 180 will, in most treatment scenarios, have a degraded physiology not shown here, including one or more of vertical compression, structural disruption of one or more walls (e.g., endplates, lateral walls). In one preferred embodiment, curable material 232a and 232b is deposited in contact against the endplates 230a and 230b of the vertebral body so that the curable material substantially interfaces with the endplates 230a and 230b and provides structural support. According to one preferred embodiment, the procedure leaves a region between the curable material deposits 232a and 232b that contains substantially no curable material. Curable material can thus be deposited in only a particular region or regions of the cavity. Physician desired localization of these deposits can be facilitated by the multi-curve device presently disclosed. For example, a physician may determine that a first deposit may best be achieved at a first curvature corresponding to a first temperature, a second deposit may best be achieved at a second curvature corresponding to a second temperature, etc. (for two or more desired curvatures and locations).

Figure 11C:
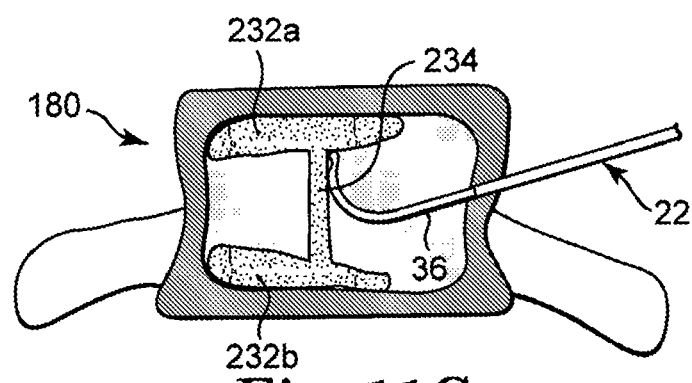

With reference to FIG. 11C, in another preferred embodiment the curable material deposits 232a and 232b can be connected by placing curable material between the curable material deposits 232a and 232b to form a curable material stabilizing column 234. In this embodiment, curable material deposits 232a and 232b are first created to stabilize the endplates of the vertebral body. A stabilizing curable material column 234 is then created between the curable material deposits 232a and 232b to connect the curable material deposits and form a curable material structure within the vertebral body. By first stabilizing the end plates, deformities created due to compression fractures can be stabilized. By stabilizing both end plates and then creating a column type structure between the end plates, the vertebral body stiffness may be significantly improved thereby minimizing issues of the overall strength of the vertebral body. Some reduced vertebral height may even be recovered or at least not allowed significant further progress thereby. Further, a physician may be able to exploit the multi-curve structure and function of the delivery cannula to help optimize location of the three deposits. For example, the first deposit 232a may best be placed using a first curvature corresponding to a first temperature, the second deposit 232b may best be placed using the same first curvature, and the intervening curable material column 234 may best be placed using a second curvature, reached by heating the needle to a second temperature.

Figure 12:
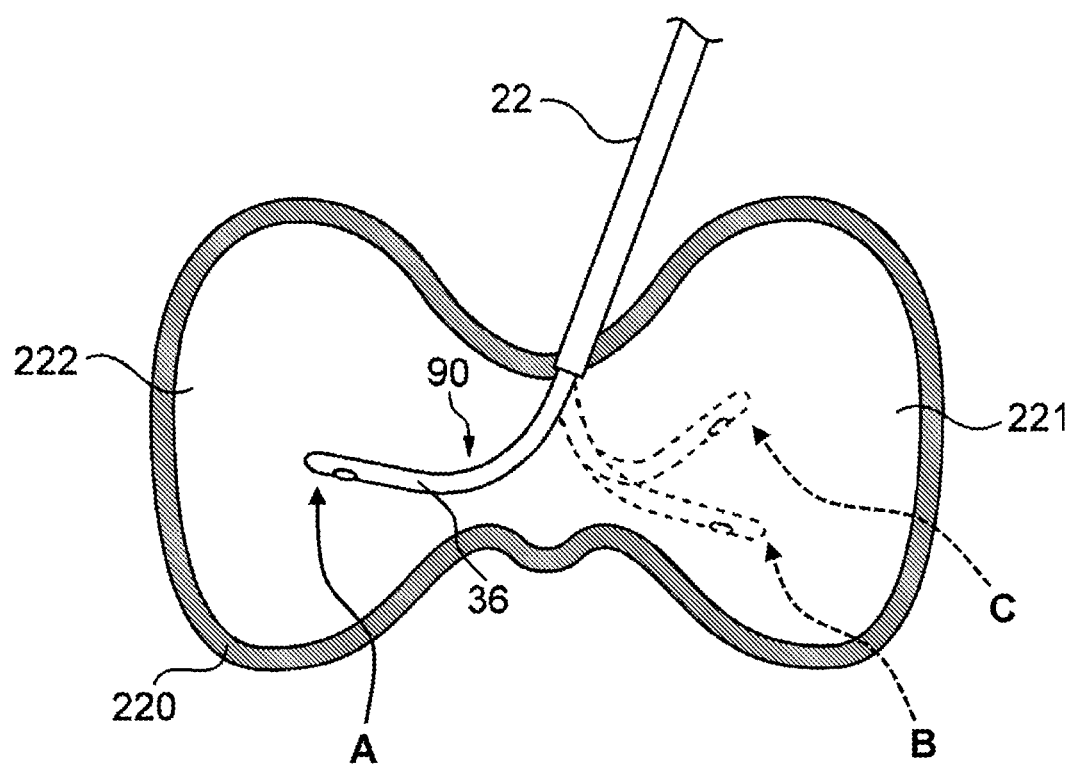
FIG. 12 is a simplified anterior view of a sacrum, illustrating use of the one device embodiment.

With reference to FIG. 12, another preferred method for delivering curable material is depicted. In this preferred embodiment, the delivery site is the sacrum 220, shown in horizontal transverse section. In this embodiment, curable material is delivered to the sacrum 220 to repair bone fragments or fractures in the sacrum. According to one preferred method of the present invention, curable material is delivered to multiple regions within the sacrum through a single access point. Preferably, a guide cannula 22 is inserted generally at the middle portion of the sacrum. As has been described above, a curvable needle is inserted into and advanced relative to the guide cannula 22. The delivery cannula 36 is preferably oriented so the curvable end 90 enters proximal to a first region 221 of the sacrum 220 after being heated to a first temperature corresponding to a first curvature shown in solid line (as "A"). Curable material is then delivered to the first region 221 of the sacrum 220. After curable material is delivered to the first region 221, the physician can then partially or fully retract the curved end 90 within the guide cannula and then re-orient the delivery cannula 36 and curved end 90. As the delivery cannula 36 is again advanced relative to the guide cannula 22, the curved end 90 enters proximal to a second region 222 within the sacrum 220. Curable material is then delivered to the second region 222 of the sacrum 220 using the same curvature (shown in dashed-line as "B"). The process can be repeated for other additional regions, such as—for example—retracting the delivery cannula 36 just into the delivery cannula, heating it to a second temperature corresponding to a second curvature and re-introducing it (into dashed-line position "C"). It should be appreciated that the retracting/heating method may be used in other embodiments as well (e.g., rather than increasing heat to change curvature while the cannula 36 is extended within the bone). Although the implantation site described above is the sacrum, fractures in other bones can be repaired by delivering curable material to multiple regions through the same access point using the above described methods Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof. For example, while specific reference has been made to vertebroplasty procedures, the devices, systems, and methods in accordance with principles of the present invention are equally applicable to delivering curable material within multiple other bones of a patient.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

We claim:

1. A cannula device configured for removing bodily material from a target site, the cannula device comprising:
a needle cannula defining:
a proximal length that is longitudinally straight s as to define a longitudinal axis, with an open proximal end;
a deflectable distal segment length
including memory metal material,
disposed opposite the proximal end, and
terminating at a distal end terminus; and
a cannula lumen extending from the open proximal end to at least one distal end region orifice,
where the deflectable distal segment length including memory metal material is temperature-dependent, being configured such that,
at a first elevated temperature, greater than an initial temperature, the memory metal is configured such that the distal segment, when unconstrained, forms a first curved shape having a first degree of curvature out of the longitudinal axis, and at a second elevated temperature, greater than the first elevated temperature, the memory metal is configured such that the distal segment, when unconstrained, forms a second curved shape having a second degree of curvature out of the longitudinal axis, different than the first degree of curvature.

2. The cannula device of claim 1, further comprising a vacuum source in fluid communication with the cannula lumen.

3. The cannula device of claim 1, where the distal orifice is configured as a side orifice open into the cannula lumen through a side of the cannula, proximal from the distal end terminus.

4. The cannula device of claim 3, further comprising an inner wire coaxially, removably disposed in the cannula lumen.

5. The cannula device of claim 1, further comprising an inner wire coaxially, removably disposed in the cannula lumen.

6. The cannula device of claim 5, where the inner wire, removably disposed in the cannula lumen, is effective to prevent coring during insertion of the cannula device through tissue.

7. The cannula device of claim 1, where the distal end terminus is configured as a non-traumatic, blunt distal end surface.

8. The cannula device of claim 7, where the distal orifice is configured as a side orifice open into the cannula lumen through a side of the cannula, proximal from the non-traumatic, blunt distal end terminus.

9. The cannula device of claim 7, where the distal end terminus is axially closed.

10. The cannula device of claim 1, where at least a portion of the deflectable distal length segment is substantially straight when constrained by a substantially straight guide cannula, when at an ambient temperature below about 38° C., or both.

11. The cannula device of claim 1, where the at least one distal end region orifice comprises a plurality of orifices.

12. A cannula device configured for removing bodily material from a target site, the cannula device comprising:
a needle cannula defining:
a proximal length that is longitudinally straight so as to define a longitudinal axis, with an open proximal end extending through a hub;
a deflectable distal segment length including memory metal material,
disposed opposite the proximal end, and
terminating at a distal end terminus; and
a cannula lumen extending from the open proximal end to at least one distal end region orifice,
wherein the deflectable segment forms a curved shape in longitudinal extension and includes a shape memory characteristic such that the deflectable segment is configured
to assume a longitudinally, substantially longitudinally straightened form generally along the longitudinal axis when subjected to a radially constraining force around the longitudinal axis and
to revert to the curved shape upon removal of the force;
where the curved shape of the deflectable segment including memory metal material is temperature-dependent, being configured such that,
at a first elevated temperature, greater than an initial temperature at which the deflectable segment including memory metal material is in its substantially longitudinally straightened form, the memory metal is configured such that the distal segment, when unconstrained, forms a first curved shape having a first degree of curvature out of the longitudinal axis, and
at a second elevated temperature, greater than the first elevated temperature, the memory metal is configured such that the distal segment, when unconstrained, forms a second curved shape having a second degree of curvature out of the longitudinal axis, greater than the first degree of curvature.

13. The cannula device of claim 12, further comprising a vacuum source in fluid communication with the cannula lumen.

14. The cannula device of claim 12, where the at least one distal end region orifice is configured as a side orifice open into the cannula lumen through a side of the cannula some distance proximal from a distal terminal end of the cannula.

15. The cannula device of claim 12, where the at least one distal end region orifice comprises a plurality of orifices.

16. The cannula device of claim 12, where the distal end terminus is configured as a non-traumatic, blunt distal end surface.

17. The cannula device of claim 16, where the distal orifice is configured as a side orifice open into the cannula lumen through a side of the cannula, proximal from the non-traumatic, blunt distal end terminus.

18. The cannula device of claim 16, where the distal end terminus is axially closed.

19. The cannula device of claim 12, where at least a portion of the deflectable distal length segment is substantially straight when constrained by a substantially straight guide cannula, when at an ambient temperature below about 38° C., or both.

20. A device configured for removing bodily material from a target site, the device comprising:
a cannula defining:
a proximal end length and extending through a hub to a proximal end terminus;
a proximal length that is longitudinally straight and that defines a longitudinal axis;
a distal deflectable segment length including memory metal material, disposed opposite the proximal end, and terminating in a distal end;
a cannula lumen extending from the proximal end, at least one distal end region orifice fluidly connected to the lumen,
wherein the deflectable segment forms a curved shape in longitudinal extension and has a shape memory characteristic such that the deflectable segment is configured
to assume a longitudinally, substantially longitudinally straightened form generally along the longitudinal axis when subjected to a radially-constraining force and
to naturally revert to the curved shape upon removal of the force;
where the curved shape of the deflectable segment including memory metal material is temperature-dependent, being configured such that, at a first elevated temperature, greater than an initial temperature at which the deflectable segment including memory metal material is in its substantially longitudinally straightened form, the memory metal is configured such that the distal segment forms a first curved shape having a first degree of curvature out of the longitudinal axis, and at a second elevated temperature, greater than the first elevated temperature, the memory metal is configured such that the distal segment forms a second curved shape having a second degree of curvature out of the longitudinal axis; and
a vacuum source in fluid communication with the cannula lumen.

21. A needle cannula device configured for removing bodily material from a target site, the cannula device comprising:
a needle cannula defining:
a longitudinally straight proximal length defining a longitudinal axis, with an open proximal end;
a deflectable distal segment length including temperature-dependent memory metal material and terminating at a distal end terminus; and
a cannula lumen extending from the open proximal end to at least one distal end region orifice;
where the deflectable distal segment length including memory metal material is configured such that:
at a first elevated temperature, greater than an initial ambient temperature, forms a first curved shape having a first degree of curvature out of the longitudinal axis, and
at a second elevated temperature, greater than the first elevated temperature, the memory metal is configured such that the distal segment, when unconstrained, forms a second curved shape having a second degree of curvature out of the longitudinal axis, greater than the first degree of curvature.

22. A cannula device configured for removing bodily material from a target site, the cannula device comprising:
a delivery cannula defining:
an open, proximal end,
a deflectable segment opposite the proximal end and terminating in a distal end;
a lumen extending from the proximal end, at least distal end region orifice fluidly connected to the lumen, wherein the deflectable segment forms a curved shape in longitudinal extension and has a shape memory characteristic such that the deflectable segment is configured (i) to assume a longitudinally, substantially straightened form when subjected to a force, (ii) to naturally revert to the curved shape upon removal of the force, (iii) to form a first curved shape having a first degree of curvature out of the longitudinal axis when at a first elevated temperature, greater than an initial ambient temperature, and (iv) to form a second curved shape having a first degree of curvature out of the longitudinal axis when at a second elevated temperature, greater than the first elevated temperature.

* * * * *